US010858397B2

(12) United States Patent
Ebben et al.

(10) Patent No.: US 10,858,397 B2
(45) Date of Patent: Dec. 8, 2020

(54) PEPTIDE INHIBITORS OF TELOMERASE TRANSLOCATION AND THERAPEUTIC USES THEREOF

(71) Applicant: THE MEDICAL COLLEGE OF WISCONSIN, INC., Milwaukee, WI (US)

(72) Inventors: Johnathan D. Ebben, Milwaukee, WI (US); Andreas M. Beyer, Menomonee Falls, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 76 days.

(21) Appl. No.: 15/756,407

(22) PCT Filed: Aug. 26, 2016

(86) PCT No.: PCT/US2016/049053
§ 371 (c)(1),
(2) Date: Feb. 28, 2018

(87) PCT Pub. No.: WO2017/040309
PCT Pub. Date: Mar. 9, 2017

(65) Prior Publication Data
US 2018/0251491 A1    Sep. 6, 2018

Related U.S. Application Data

(60) Provisional application No. 62/211,524, filed on Aug. 28, 2015.

(51) Int. Cl.
| | | |
|---|---|---|
| *A61K 38/00* | (2006.01) | |
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *A61K 38/10* | (2006.01) | |
| *A61K 38/16* | (2006.01) | |
| *A61P 9/00* | (2006.01) | |
| *C07K 7/08* | (2006.01) | |
| *A61K 47/60* | (2017.01) | |
| *C07K 14/00* | (2006.01) | |
| *A61K 38/43* | (2006.01) | |
| *A61K 9/00* | (2006.01) | |
| *A61P 35/00* | (2006.01) | |

(52) U.S. Cl.
CPC ............ *C07K 7/08* (2013.01); *A61K 9/0019* (2013.01); *A61K 38/16* (2013.01); *A61K 38/43* (2013.01); *A61K 47/60* (2017.08); *C07K 14/00* (2013.01); *A61K 38/10* (2013.01); *A61P 9/00* (2018.01); *A61P 35/00* (2018.01)

(58) Field of Classification Search
None
See application file for complete search history.

(56) References Cited

U.S. PATENT DOCUMENTS

| 2010/0003229 A1 | 1/2010 | Santos |
| 2010/0074925 A1 | 3/2010 | Carmon |

FOREIGN PATENT DOCUMENTS

| EP | 1 994 942 | 11/2008 |
| EP | 2 899 200 | 7/2015 |
| WO | 2014012683 A1 | 1/2014 |

OTHER PUBLICATIONS

"Homology", Encyclopedia Britannica, available online at www.britannica.com/print/article/270557, 2 pages at p. 1, 1st paragraph (accessed on Jul. 22, 2018) (Year: 2018).*
Pearson et al., Curr. Protoc. Bioinformatics, 9 pages (2013) (Year: 2013).*
Kanduc, J. Pept. Sci. 18:487-494 (2012) (Year: 2012).*
Samudrala, R., "Difference Between Homology, Identity, and Similarity," available online at http://www.bio.net/mm/proteins/1998-July/006538.html, 1 page (1998) (Year: 1998).*
Dephoure et al., Molec. Biol. Cell 24:535-542 (2013) (Year: 2013).*
Cambridge English Dictionary, "Prevent," available online at https://dictionary.cambridge.org/us/dictionary/english/prevent, 8 pages (accessed online Jul. 20, 2019) (Year: 2019).*
Cell Signaling Technology, "Post-translational Modification of Amino Acids," available online at https://media.cellsignal.com/www/pdfs/content-fragments/gu-nt2-amino-acid-poster.pdf, 1 page (2015) (Year: 2015).*
Ciesla et al., Acta Biochim Polonica 58:137-147 (2011) (Year: 2011).*
UniProt Accession No. 014746, 28 pages (1998) (Year: 1998).*
NCBI Database, GenBank Accession No. AH007699.2, 13 pages (last updated 2016 but first available 1999) (Year: 1999).*
Roberts et al., Adv. Drug Delivery Rev. 64:116-127 (2012) (Year: 2012).*
Betts et al., Bioinformatics for Geneticists, Barnes et al., eds., John Wiley & Sons, Ltd., p. 289-316 (2003) (Year: 2003).*
The International Search Report and Written Opinion for International Patent Application No. PCT/US2016/049053 dated Dec. 23, 2016.
Pascolo, E., et al: "Mechanism of human telomerase inhibition by BIBR1532, a synthetic, non-nucleosidic drug candidate", Journal of Biological Chemistry, American Society for Biochemistry and Molecular Biology, US, vol. 277, No. 18, May 3, 2002 (May 3, 2002), pp. 15566-15572.

(Continued)

*Primary Examiner* — Thea D'Ambrosio
(74) *Attorney, Agent, or Firm* — Quarles & Brady LLP

(57) ABSTRACT

This disclosure provides compositions and methods for treating or preventing cardiac or vascular toxicity in a subject receiving a chemotherapeutic agent, where the cardiac or vascular toxicity is associated with administration of the chemotherapeutic agent. Also provided are compositions and methods for treating or preventing endothelial dysfunction and for modulating endothelial function and oxidative stress.

22 Claims, 13 Drawing Sheets
(2 of 13 Drawing Sheet(s) Filed in Color)

Specification includes a Sequence Listing.

(56) References Cited

OTHER PUBLICATIONS

Ait-Aissa, Karima, et al: "Friend or foe? Telomerase as a pharmacological target in cancer and cardiovascular disease", Pharmacological Research, vol. 111, Jul. 6, 2016 (Jul. 6, 2016), pp. 422-433.
European Patent Office, Examination Report for application 16762938.5. dated Nov. 13, 2019.
IP Australia. Examination Report No. 1 for application 2016316774. dated Feb. 24, 2020.
Zhang, X., et al. "Telomere shortening and apoptosis in telomerase-inhibited human tumor cells." Genes & development 13.18 (1999): 2388-2399.

* cited by examiner

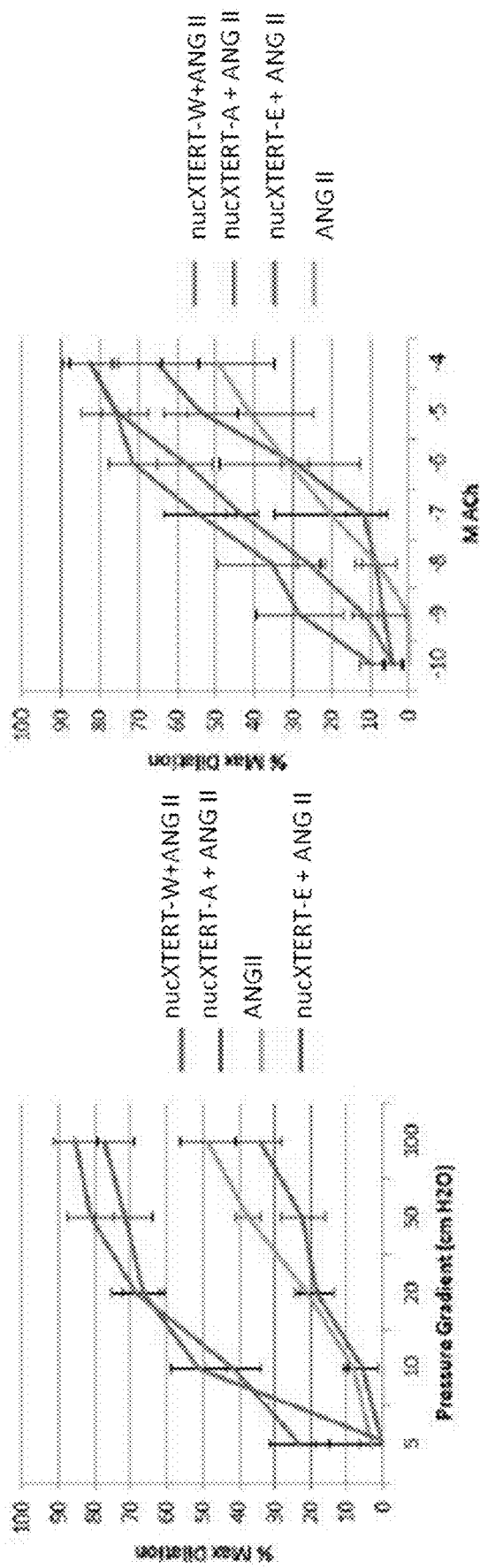
FIGS. 5A-5C, CONTINUED

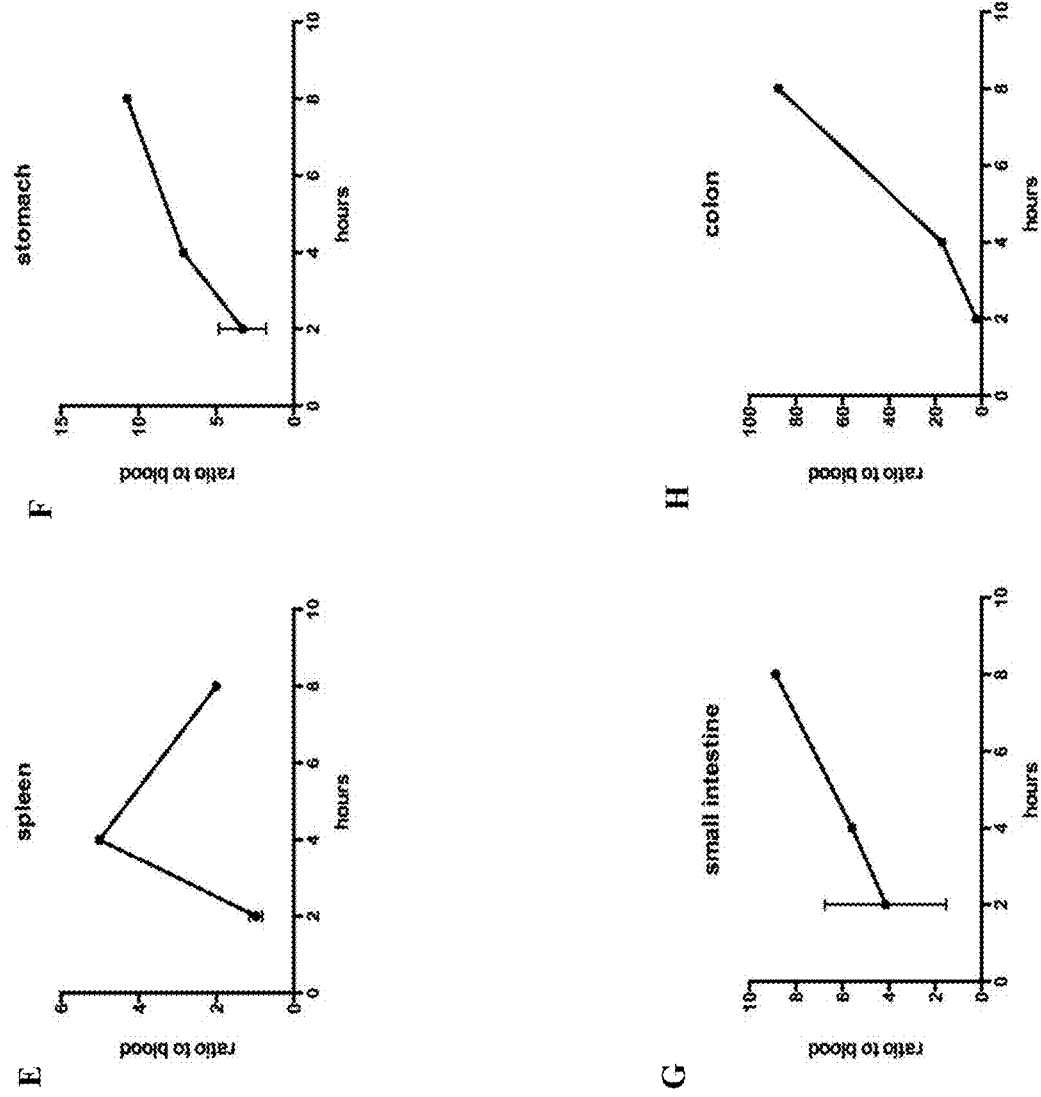
FIGS. 8A-8L, CONTINUED

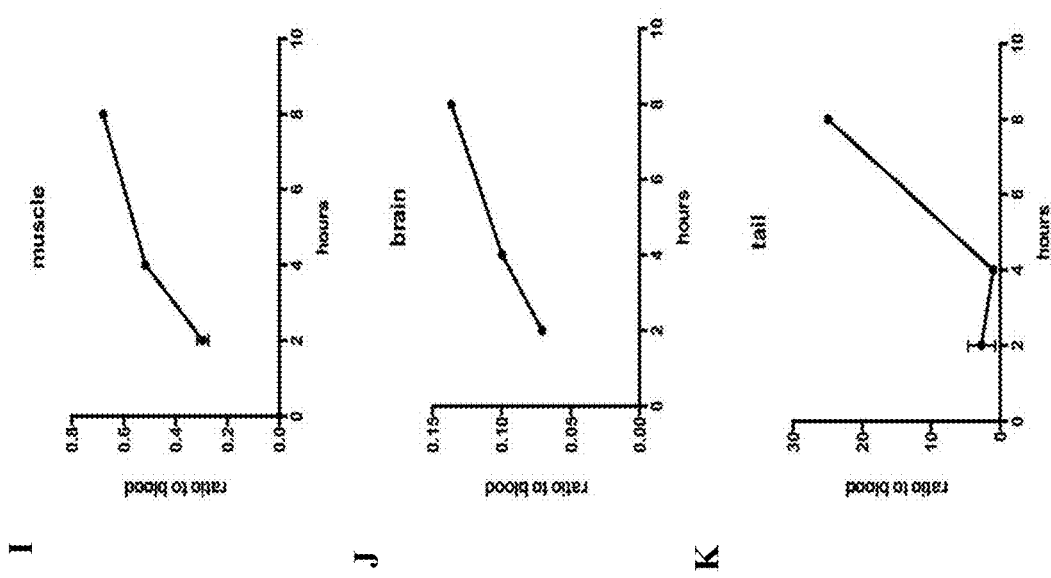
FIGS. 8A-8L, CONTINUED

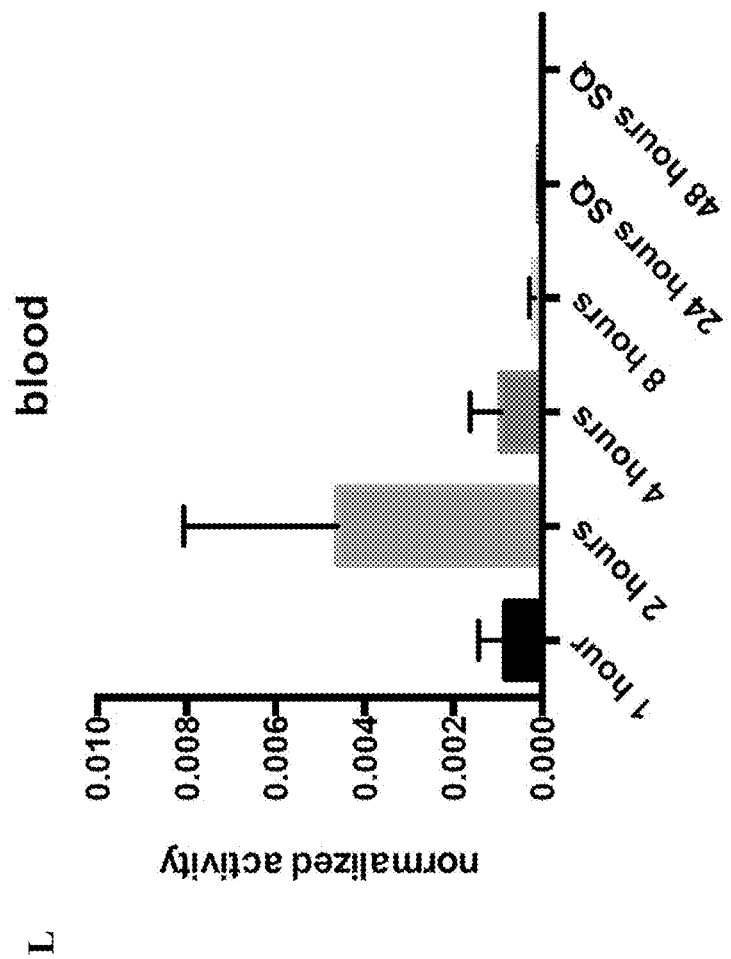
FIGS. 8A-8L, CONTINUED

PEPTIDE INHIBITORS OF TELOMERASE TRANSLOCATION AND THERAPEUTIC USES THEREOF

CROSS-REFERENCE TO RELATED APPLICATIONS

This application represents the national stage entry of PCT International Application No. PCT/US2016/049053 filed on Aug. 26, 2016 and claims priority to, and the benefit of, U.S. Provisional Patent Application Ser. No. 62/211,524, filed Aug. 28, 2015, which are incorporated herein by reference in its entirety for all purposes.

STATEMENT REGARDING FEDERALLY SPONSORED RESEARCH

Not applicable.

BACKGROUND

Overexpression of telomerase is associated with cardiac and vascular protection; however, re-activation of the telomerase enzyme in certain cell types may also be an important event in oncogenic transformation, given the role of telomerase in cellular immortalization and proliferation. The mechanisms that underlie the beneficial effects of telomerase reactivation in the prevention and amelioration of cardiac and vascular diseases have to this point been unclear.

Accordingly, it would be beneficial to develop compositions and therapeutic and prophylactic methods that overcome the deficiencies of standard protocols and provide new treatment paradigms for vascular diseases while mitigating adverse or off-target side effects of chemotherapeutic cancer treatments. A need exists for compositions and methods to achieve the aforementioned goals.

SUMMARY OF THE INVENTION

The present invention overcomes the aforementioned drawbacks by providing compositions and methods as described herein.

In a first aspect, provided herein is an isolated peptide comprising an amino acid sequence at least 80% homologous to the sequence as set forth by: by SEQ ID NO:6 (RRRGGX$_1$ASRSLPLPKRPRR), where X$_1$ is a phosphomimetic residue selected from the group consisting of as aspartic acid and glutamic acid, the isolated peptide being capable of preventing TERT nuclear translocation, wherein said isolated peptide is less than 20 amino acids. The isolated peptide can have the sequence forth as SEQ ID NO:2. The peptide can be blood brain barrier (BBB)-permeant.

In another aspect, provided herein is an isolated polynucleotide comprising a nucleic acid sequence encoding a peptide comprising an isolated peptide as provided herein.

In another aspect, provided herein is an isolated peptide comprising a non-phosphorylatable substitution relative to the serine residue at position 6 of SEQ ID NO:1, where said isolated peptide is less than 20 amino acids, comprises an amino acid sequence at least 80% homologous to the sequence as set forth by SEQ ID NO:1, and is capable of preventing TERT nuclear translocation. The isolated peptide can have the sequence set forth as SEQ ID NO:3. The peptide can be BBB-permeant. Also provided herein is an isolated polynucleotide comprising a nucleic acid sequence encoding a peptide comprising the comprising a non-phosphorylatable substitution relative to the serine residue at position 6 of SEQ ID NO:1.

In yet another aspect, provided herein is a method of preventing nuclear translocation of a telomerase enzyme in a human cell, the method comprising contacting the human cell to a inhibitor of TERT nuclear translocation. The inhibitor of TERT nuclear translocation can be a peptide. The inhibitor can be a peptide comprising a sequence selected from the group consisting of SEQ ID NO:2, SEQ ID NO:3, and SEQ ID NO:4. The inhibitor can be a peptide having a sequence selected from the group consisting of SEQ ID NO:2, SEQ ID NO:3, and SEQ ID NO:4. The administration can be parenteral administration.

In a further aspect, provided herein is a method of reducing adverse cardiac effects in a subject, the method comprising administering a therapeutically effective amount of an inhibitor of TERT nuclear translocation to a subject, wherein administering the synthetic peptide reduces occurrence of adverse cardiac effects in the subject. The adverse cardiac effects can be cardiotoxicity associated with administration of a chemotherapeutic agent to the subject. The subject will receive or is receiving a chemotherapeutic agent. The inhibitor of TERT nuclear translocation can be a peptide. The peptide can have a sequence selected from the group consisting of SEQ ID NO:2, SEQ ID NO:3, and SEQ ID NO:4. The administration can be parenteral administration. In some cases, also provided herein is a method for antagonizing the adverse cardiac effects of angiotensin II (ANG II), which causes significant cardiac and vascular damage and is associated with hypertension and many other CV disease states.

In another aspect, provided herein is a method of treating a hyperproliferative disease in a subject, the method comprising administering to the subject a therapeutically effective amount of an isolated peptide into the subject, wherein said isolated peptide is less than 20 amino acids and comprises an amino acid sequence at least 80% homologous to the sequence as set forth by SEQ ID NO:6 (RRRGGX$_1$ASRSLPLPKRPRR); where X$_1$ is a phosphomimetic residue selected from the group consisting of as aspartic acid and glutamic acid, relative to the corresponding position in SEQ ID NO:1, the isolated peptide being capable of preventing TERT nuclear translocation, thereby treating the hyperproliferative disease. The hyperproliferative disease can be cancer. The peptide can comprise an amino acid sequence as set forth in SEQ ID NO:3. The peptide can be PEGylated. The PEGylated peptide can comprise the sequence set forth in SEQ ID NO:4.

Also provided herein is a method of reducing oxidative stress, the method comprising administering to a subject an effective amount of an inhibitor of TERT nuclear translocation. The inhibitor of TERT nuclear translocation can be a peptide. The peptide can comprise a sequence selected from the group consisting of SEQ ID NO:2, SEQ ID NO:3, and SEQ ID NO:4.

In a further aspect, provided herein is a method of preventing mitochondrial translocation of a telomerase (TERT) enzyme in a human cell, the method comprising contacting the human cell to a inhibitor of TERT mitochondrial translocation. The inhibitor can be a peptide comprising SEQ ID NO:5.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

This patent application file contains at least one drawing executed in color. Copies of this patent application publication with color drawings will be provided by the Office upon request and payment of the necessary fee.

DETAILED DESCRIPTION OF THE INVENTION

Figures 1A, 1B:
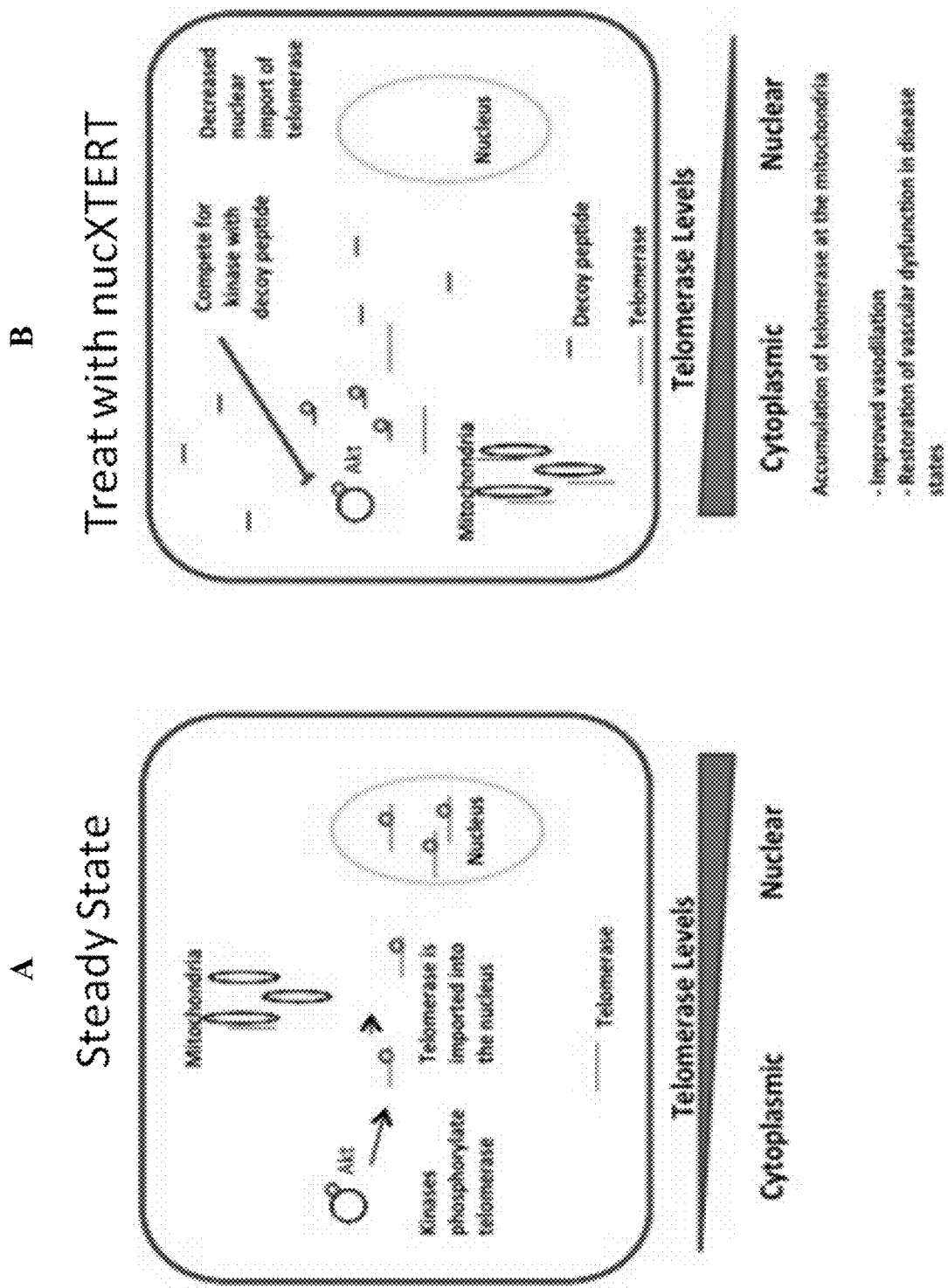
FIGS. 1A-1B show that, under normal conditions, telomerase is phosphorylated at the NLS by kinases including Akt, leading to nuclear import. (A) Telomerase is primarily localized to the nucleus. (B) nucXTERT serves as a decoy peptide, competing with the telomerase for the kinases involved in phosphorylating the NLS. This results in decreased nuclear import of telomerase and accumulation of telomerase in the cytoplasm and mitochondria.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

In General

While it was known that TERT dysregulation play an important role in many vascular disease phenotypes, including vascular dysfunction associated with coronary artery disease (CAD), and that TERT expression confers cardioprotection in the adult mouse heart after MI, global inhibition of TERT function in the context of cancer results in off-target toxicities, including vascular and cardiac damage.

The compositions and methods provided herein are based at least in part on the discovery that TERT accumulation in the nucleus is significantly attenuated following peptide inhibitor administration. It was further discovered that mitochondrial-associated telomerase, and not nuclear telomerase, is the cause of cardiovascular protection associated with telomerase activity, while NLS peptide inhibitors protect isolated human vessels from damage in response to stress and may decrease migration of lung tumor cells. Inhibition of nuclear transport of TERT, the catalytic subunit of telomerase, increases cytoplasmic (including mitochondrial) telomerase localization and activity. Therefore, provided herein are compositions and methods that harness the benefits of telomerase overexpression in cardiac and vascular disease without increasing cancer risk, and also provide improved means of inhibiting nuclear telomerase in cancer in a manner that is less toxic. NLS peptide inhibitor compositions provided herein can be used in combination with traditional and targeted cancer therapies to minimize toxicity to the vasculature and heart.

Compositions

In a first aspect, provided herein is a synthetic peptide or plurality of synthetic peptides comprising a telomerase nuclear localization signal (NLS) or mitochondria localization signal (MLS), where the synthetic peptide can effectively compete with endogenous localization signals for modification by kinases within the cell. The NLS-containing peptide compositions and MLS-containing peptide compositions described herein are believed to be the first telomerase inhibitors that specifically inhibit only the nuclear and mitochondrial functions of TERT, respectively.

In some cases, the synthetic peptide is an inhibitor of TERT nuclear localization/translocation. The peptides described herein are believed to be the first telomerase inhibitors that specifically inhibit only the nuclear function of TERT. By mimicking TERT's nuclear localization signal, the inhibitory peptide blocks or attenuates the ability of endogenous telomerase to move from the cytosol to the nucleus.

In other cases, the synthetic peptide is an inhibitor of TERT mitochondrial localization. By mimicking TERT's mitochondrial localization signal, the inhibitory peptide blocks or attenuates the ability of endogenous telomerase to move from the cytosol into mitochondria.

As described herein, the synthetic peptides of the invention are blood-brain barrier (BBB) permeant peptides. BBB permeant peptides are characterized by the ability of the peptide to penetrate the blood brain barrier formed by brain capillary endothelial cells. As used herein, the term "blood-brain barrier" or "BBB" refers to that obstacle to biological transport of drugs, ions, peptides, proteins and toxins that is formed by the membrane properties, structure and tight junctions of brain capillary endothelial cells.

As used herein, the term "peptide" is broadly defined to include any organic compound consisting of two or more amino acids joined by a chemical bond in which the amino group of one amino acid combines with the carboxyl group of a second amino acid. As used herein, the term "amino acid" is broadly defined to include naturally occurring amino acids as well as non-naturally occurring amino acids, including amino acid analogs and derivatives, such as molecules containing an amino acid moiety. As used herein, the term amino acid therefore embraces, for example, naturally occurring proteogenic L-amino acids; D-amino acids; chemically modified amino acids such as amino acid analogs and derivatives; naturally occurring non-proteogenic amino acids such as norleucine, β-alanine, ornithine, etc.; and chemically synthesized compounds having properties known in the art to be characteristic of amino acids, including non-native β-amino acids, those containing non-natural side chains, and D-amino acids as well as inverso and retro-inverso peptide sequences.

In some cases, the synthetic peptide is a phosphomimetic peptide, meaning the peptide comprises a "phosphomimetic" amino acid, e.g., an aspartic acid (D), or a glutamic acid (E), in place of a naturally-occurring phosphorylated amino acid. Within cells, proteins are commonly modified at serine, tyrosine, and threonine amino acids by adding a phosphate group. Phosphomimetic (also called "phospho-mimicking") peptides of the invention can be obtained through substitution of a phosphorylated residue (e.g., a serine residue) with a negatively charged amino acid residue (to mimic the negative charge of the phosphate group), such as aspartic acid (D) or glutamic acid (E). Aspartic acid and glutamic acid are chemically similar to phosphorylated serine ("phospho-serine"). When, for example, an aspartic acid replaces a serine, it is a phosphomimetic of phospho-serine and the resulting peptide is always in its phosphorylated form and, thus, constitutively active. In some cases, a phosphomimetic peptide as provided herein has the amino acid sequence set forth as SEQ ID NO:2 (RRRGGEASRSLPLPKRPRR). This peptide, referred to as nucXTERT-E in the Examples section, comprises a glutamic acid (E) in place of the serine residue found at position 6 of SEQ ID NO:1) (RRRGGSASRSLPLPKRPRR). In other cases, a phosphomimetic peptide as provided herein has the amino acid sequence set forth as SEQ ID NO:7 (RRRGGDASRSLPLPKRPRR), where the peptide comprises an aspartic acid (D) in place of the serine residue found at position 6 of SEQ ID NO:1. The serine at position 6 of SEQ ID NO:1 (referred to as nucXTERT/nucXTERT-W in the Examples section) corresponds to position 227 of the amino acid sequence encoding telomerase enzyme (OMIM ID 187270; GenBank: AAD30037.1). Phosphorylation of the serine at position 227 of the wild-type telomerase sequence enables nuclear import of telomerase.

In some cases, the synthetic peptide is an isolated peptide comprising an amino acid sequence at least 80% (e.g., at least 80%, 85%, 90%, 95%, 99%) homologous to the sequence as set forth by: by SEQ ID NO:6 (RRRGGX$_1$ASRSLPLPKRPRR); where X$_1$ is a phosphomimetic residue selected from the group consisting of as aspartic acid and glutamic acid, the isolated peptide being capable of preventing TERT nuclear translocation, wherein said isolated peptide is less than 20 amino acids.

According to specific embodiments, phosphomimetic peptides as described herein are provided for use as a medicament or for use in conjunction with one or more therapeutics. According to more specific embodiments, such phosphomimetic peptides are provided to reduce or mitigate oxidative stress, or for use in the treatment of cancer or in the treatment of cardiac and/or vascular disease, including peripheral vascular diseases. Peripheral vascular diseases include, without limitation, hypertrophy, diabetic retinopathy, diseases of the adipose vessels and other vascular beds.

In other cases, a synthetic peptide provided herein is phospho-deficient, where an amino acid substitution removes a phosphorylated amino acid from the resulting peptide or polypeptide. For example, a phospho-deficient peptide can comprise a substitution of a non-phosphorylatable amino acid residue such as alanine in place of a phosphorylated amino acid in the peptide sequence set forth in SEQ ID NO:1. In a particular embodiment, a phospho-deficient synthetic peptide as provided herein has the amino acid sequence set forth as SEQ ID NO:3 (RRRGGAASRSLPLPKRPRR). This peptide, referred to as nucXTERT-A in the Examples section, comprises an alanine (A) in place of the serine residue found at position 6 of SEQ ID NO:1)(RRRGGSASRSLPLPKRPRR). As described above, the serine at position 6 of SEQ ID NO:1 (referred to as nucXTERT/nucXTERT-W in the Examples section) corresponds to position 227 of the amino acid sequence encoding telomerase enzyme (OMIM ID 187270; GenBank: AAD30037.1).

In some cases, the synthetic peptides provided herein comprise a poly(ethylene glycol) moiety. Such peptides are referred to herein as PEGylated peptides. As used herein, the term "PEGylated" refers to the covalent attachment of poly(ethylene glycol) ("PEG") residue to a peptide as provided herein by PEGylation. In some cases, peptides are PEGylated at the N- and/or C-terminus to increase biostability and cell permeability. For example, a synthetic peptide of the invention can have a PEGylated amino acid sequence as set forth in SEQ ID NO:4 (Ac-CGGRRRG-GEASRSLPLPKRPRR-peg12-amide, where "Ac" refers to acetylation, which can increase peptide stability by preventing N-terminal degradation). The acetylation of a peptide's N-terminal cysteine forms the derivative N-acetyl-L-cysteine.

As used herein, the term "PEGylation" means a covalent linkage of a poly(ethylene glycol) residue at the N-terminus of the polypeptide and/or an internal lysine residue. PEGylation of proteins is widely known in the state of the art and is reviewed by, for example, Veronese, F. M., Biomaterials 22 (2001) 405-417. PEG can be linked using different functional groups and polyethylene glycols with different molecular weight, linear and branched and forked PEGS as well as different linking groups (see also Francis, G. E., et al., *Int. J. Hematol.* 68 (1998) 1-18; Delgado, C., et al., *Crit. Rev. Ther. Drug Carrier Systems* 9 (1992) 249-304). The terms "PEG", "polyethylene glycol", or "poly(ethylene glycol)" as used herein refer to any water soluble poly(ethylene oxide), and includes molecules comprising the structure —(CH$_2$CH$_2$O)$_n$— where n is an integer from 2 to about 800. A commonly used PEG is end-capped PEG, wherein one end of the PEG is capped with a relatively inactive group such as an alkoxy while the other end is a hydroxyl group that may be further modified. An often used capping group is methoxy, and the corresponding end-capped PEG is often denoted mPEG. The notion PEG is often used instead of mPEG.

Generally, PEG polymer molecules used in a PEGylation reaction have a molecular weight of about 10 kDa to 40 kDa (by "molecular weight" as used herein there is to be understood the mean molecular weight of the PEG because PEG as a polymeric compound is not obtained with a defined molecular weight but in fact has a molecular weight distribution; the term "about" indicates that in said PEG preparations, some molecules will weigh more and some less than the indicated molecular weight, i.e., the term about refers to a molecular weight distribution in which 95% of the PEG molecules have a molecular weight within +/−10% of the indicated molecular weight).

PEG is a well-known polymer with good solubility in many aqueous and organic solvents, which exhibits low toxicity, lack of immunogenicity, and is clear, colorless, odorless, and stable. For these reasons and others, PEG has been selected as the preferred polymer for attachment, but it has been employed solely for purposes of illustration and not limitation. Similar products may be obtained with other water-soluble polymers, including without limitation; polyvinyl alcohol, other poly(alkylene oxides) such as poly(propylene glycol) and the like, poly(oxyethylated polyols) such as poly(oxyethylated glycerol) and the like, carboxymethylcellulose, dextran, polyvinyl alcohol, polyvinyl purrolidone, poly-1,3-dioxolane, poly-1,3,6-trioxane, ethylene/maleic anhydride, and polyaminoacids. One skilled in the art will be able to select the desired polymer based on the desired dosage, circulation time, resistance to proteolysis, and other considerations.

A wide variety of PEG derivatives are both commercially available and suitable for use in the preparation of the PEG-conjugated peptides of the invention. Suitable PEG derivatives are activated PEG molecules with an average molecular weight of from about 5 to about 40 kDa, in one embodiment from about 20 to about 40 kDa, preferably about 30 kDa to about 35 kDa. The PEG derivative is in one embodiment a linear or a branched PEG. A wide variety of PEG derivatives suitable for use in the preparation of PEGylated peptides as provided herein can be obtained from Shearwater Polymers (Huntsville, Ala., U.S.A.; nektar.com on the World Wide Web).

In other cases, a synthetic peptide provided herein can comprise a myristoyl group by myristoylation. As used herein, the terms "myristoylated" and "myristoylation" refer to a lipidation modification in which a myristoyl group, derived from myristic acid, is covalently attached by an amide bond to the alpha-amino group of an N-terminal glycine residue. The myristoyl group is a 14-carbon saturated fatty acid (C14), which gives the protein sufficient hydrophobicity and affinity for membranes, but not enough to permanently anchor the protein in the membrane. Generally, N-myristoylation therefore acts as a conformational localization switch, in which protein conformational changes influence affinity of a peptide or polypeptide for membrane attachment. Because of this conditional localization, signal proteins that selectively localize to membrane, such as Src-family kinases, are N-myristoylated.

Other peptide modifications appropriate for use with the peptides provided herein include, without limitation, glycosylations, acetylations, phosphorylations, as well as the addition of peptide linkers such as a cysteine linker or spacer. Peptide modifications can occur at the N-terminal and/or C-terminal ends of a peptide. For example, the amino and/or carboxy termini of a peptide can be modified produce other compounds of the invention. Amino terminus modifications include methylation (i.e., —NHCH$_3$ or —N(CH$_3$)$_2$), acetylation (e. g., with acetic acid or a halogenated derivative thereof such as a-chloroacetic acid, a-bromoacetic acid, or a-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In preferred embodiments, the N-terminus is acetylated. In most preferred embodiments an N-terminal glycine is acetylated to yield N-acetylglycine (AcG).

In some cases, spacers or linkers such as cysteine (Cys) linkers are used to attach various moieties (e.g., radiolabel-binding moiety, chelating moiety, spacer moiety) or cargo molecules (e.g., a nucleic acid, peptide nucleic acid (PNA), phosphorodiamidate morpholino oligonucleotide (PMO), locked nucleic acid (LNA), antisense oligonucleotide, short interfering RNA (siRNA), peptide, cyclic peptide, protein, antibody, or drug) to a peptide provided herein. For example, peptides can be covalently linked to a radiolabel-binding moiety that is stably complexed with a radioisotope such as, for example, technetium-99m. Generally, linker sequences allow chemical linkage of the peptide to a cargo molecule.

In some cases, linker sequences act as a spacer to separate the peptide from the cargo. With respect to Cys-containing linker sequences, cysteine residues permits formation of a disulphide, thioether or thiol-maleimide linkage. Preferably, amino acid spacers and cargo molecules are chemically linked by covalent bonds.

In another aspect, provided herein is a synthetic peptide that is an inhibitor of TERT mitochondrial localization. By mimicking TERT's mitochondrial localization signal, the inhibitory peptide blocks or attenuates the ability of endogenous telomerase to move from the cytosol into mitochondria. In some cases, the synthetic peptide that inhibits TERT mitochondrial localization is peptide having the amino acid sequence as set forth in SEQ ID NO:5 (MPRAPRCRAVRSLLRSHYRE). This peptide is referred to as mitoXTERT in the Examples section.

The peptides of the present invention can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides and/or polypeptides of the present invention. These techniques may be preferred when the peptide is linked to a heterologous protein (i.e. a fusion protein) since recombinant techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Examples of heterologous proteins are provided hereinbelow.

To produce a peptide and/or polypeptide of the present invention using recombinant technology, a polynucleotide encoding the nuclear targeting peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

Other than containing the necessary elements for the transcription and translation of the inserted coding sequence (encoding the polypeptide), the expression construct of the present invention can also include sequences engineered to optimize stability, production, purification, yield or activity of the expressed peptide.

Thus, peptides and/or polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing, and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site (e.g., see Booth et al., Immunol. Lett. 19:65-70 (1988); and Gardella et al., J. Biol. Chem. 265:15854-15859 (1990)).

The peptides and/or polypeptides of the present invention are preferably retrieved in "substantially pure" form. As used herein, the phrase "substantially pure" refers to a purity that allows for the effective use of the protein in the applications described herein.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

Methods of Use

Provided herein are therapeutic methods employing one or more TERT localization inhibitors described herein.

In one aspect, provided herein is a method for reducing cardiotoxicity associated with cancer treatment (e.g., treatment with a chemotherapeutic agent), where the method comprises or consists essentially of administering an inhibitor of TERT nuclear translocation to a subject prior to or during administration of a chemotherapeutic agent. In some cases, the inhibitor of TERT nuclear localization is administered in conjunction with, sequentially or simultaneously, one or more chemotherapeutic agents to reduce the cardiac and vascular toxicities associated with such chemotherapeutic agents. Chemotherapeutic agents associated with cardiac and vascular toxicities include, without limitation, those that inhibit telomerase, as well as doxorubicin and tyrosine kinase inhibitors. Anti-cancer drugs that do not directly target TERT may generally inhibit the enzyme, resulting in off-target effects. Administration of the inhibitor of TERT nuclear localization reduces cardiac and vascular toxicities that are otherwise dose-limiting.

Nuclear telomerase activity is important for activation of cellular and tumor autophagy, which is a key chemotherapy resistance mechanism that renders many tumors less sensitive to chemotherapy. Without being bound by any particular mechanism or mode of action, it is believed that NLS peptide inhibitors and other inhibitors of TERT nuclear localization preserve mitochondrial TERT function while reducing or abolishing nuclear function of telomerase. As described in the Examples, the nuclear function of telomerase is important for cell transformation and tumorigenesis. Accordingly, administration of inhibitors of TERT nuclear localization to a subject receiving chemotherapy may increase the efficacy of the chemotherapeutics while protecting cardiac and vascular tissue from chemotherapy associated toxicity.

In another aspect, provided herein is a method for mitigating oxidative stress and metabolic effects associated with oxidative stress, where the method comprises or consists essentially of administering to a subject a therapeutically effective amount of a peptide that inhibits TERT nuclear localization provided herein, whereby administration of the peptide boosts mitochondrial function. Without being bound by any particular mechanism or mode of action, it is believed that NLS peptide inhibitors and other inhibitors of TERT nuclear localization reduce oxidative stress and reduce mitochondrial DNA damage. As a means of mitigating oxidative stress, the peptides and their derivatives described herein may have utility in the treatment and amelioration of diseases with a significant oxidative stress component, including Parkinson's disease, Amytrophic Lateral Sclerosis (ALS), Alzheimer's disease, and other neurodegenerative conditions.

In a further aspect, provided herein is a method for reducing or ameliorating the negative vasoconstrictive effects associated with administration of Angiotensin II, where the method comprises or consists essentially of administering a peptide that inhibits TERT nuclear localization provided herein to a subject prior to, during, or following administration of Angiotensin II. As described in the Examples that follow, coronary and adipose vessels are less susceptible to the vasoconstrictive properties of Angiotensin II in the presence of the NLS peptide inhibitors described herein. ANG II is elevated in many different pathologies, including some hypertensive states. As such, the peptide inhibitors and their derivatives described herein may be useful in the treatment of chronic and acute hypertension.

In another aspect, provided herein is a method for reducing adverse or off-target effects of tyrosine kinase inhibitor (TKI) therapy in a subject receiving TKI therapy. In some malignancies such as chronic myeloid leukemia, persistent tyrosine kinase inhibitor therapy maintains long remissions. However, it is increasingly appreciated that the TKIs have vascular side effects as patients continue to live longer. In addition, TKI therapy ultimately fails over the course of many years, possibly because tumor cells are able to evade destruction by TKI therapy by inducing autophagy. The method for reducing adverse or off-target effects of TKI comprises or consists essentially of administering an inhibitor of TERT nuclear localization to a subject in need thereof, whereby administration prevents, treats, or ameliorates off-target effects of TKIs on the vasculature.

In another aspect, provided herein is a method of treating or preventing tumor metastasis. Also provided is a method for decreasing or inhibiting tumor cell migration. The methods comprise or consist essentially of administering an inhibitor of TERT nuclear localization to a subject in need thereof, whereby administration prevents, treats, or ameliorates off-target effects of TKIs on the vasculature.

In another aspect, provided herein is a method of treating a cardiac disorder. Administration of an inhibitor of TERT nuclear localization is effective to treat or prevent cardiac conditions or disorders including, without limitation, coronary artery disease, hypertension, and myocardial infarct. Accordingly, provided herein is a method of preventing or treating a cardiac disorder or condition, where the method comprises or consists essentially of administering an inhibitor of TERT nuclear translocation to a subject predisposed exertion-related myocardial infarction, to a subject predisposed to the cardiac disorder as a result of impaired flow-mediated vascular dilation following myocardial infarction, to a subject having coronary artery disease (CAD), to a subject having normal cardiac vessels to present onset of the cardiac disorder or condition. In some cases, the method further comprises treating a subject following myocardial infarction (MI).

In another aspect, provided herein is a method of preventing or treating endothelial dysfunction, where the method comprises or consist essentially of administering to a subject a therapeutically effective amount of an inhibitor of TERT nuclear localization. Endothelial dysfunction is characterized by a loss of barrier function and an infiltration of cellular material into the vascular wall and loss of physiological vascular tone. As used herein, references to "treating endothelial dysfunction" are to be considered as references to improvement of endothelial function in treatment of disorders which are related to endothelial dysfunction. Such disorders include both macrovascular disorders (relating to the large blood vessels) such as transient ischemic attack, stroke, angina, myocardial infarction, cardiac failure, and peripheral vascular disease, as well as microvascular disorders (relating to the small blood vessels) such as diabetic retinopathy (non-proliferative, proliferative, macular oedema), microalbuminuria, macroalbuminuria, end stage renal disease, erectile dysfunction, autonomic neuropathy, peripheral neuropathy, osteomyelitis and lower limb ischemia. Administration of an inhibitor of TERT nuclear localization can improve endothelial function in the subject and, in some cases, treat angina induced by vasospasm of damaged vessels. Other diseases and conditions for which the methods provided herein are particularly useful include those associated with endothelial dysfunction. Such diseases and conditions include, without limitation, diabetes, dyslipidemia, hypertension, myocardial infarction, cardiovascular disease, coronary artery disease (CAD), microvessel disease, ischemic disease, peripheral artery disease, angina induced by vasospasm (e.g., Prinzmetal's angina), preeclampsia, and chronic renal disease. Treatment according to the method treats or prevents chronic cardiac and vascular pathologies that involve endothelial dysfunction.

Preferably, the method prevents or treats coronary endothelial dysfunction (CED). In some cases, the subject is diagnosed as having or is suspected of CED and, as a result, is identified as in need to treatment to prevent or reduce the risk of experiencing coronary conditions or CAD. Once identified as having CED, or suspected of having CED, a subject can be treated with inhibitor of TERT nuclear localization to prevent or reduce the risk of developing a CAD event.

In some cases, an inhibitor of TERT nuclear localization is administered one or more times over defined period of time. In preferred embodiments, short term administration of the inhibitor is appropriate. In other cases, targeted delivery of the inhibitor of TERT nuclear localization is preferable to limit systemic exposure upon administration to the subject.

Effective amounts of therapeutic agents can depend on various factors, such as the activities of the particular agents used, the frequency of administration, the duration of treatment, the severity of the condition being treated, and the condition and prior medical history of the mammal being treated. A dose that is lower than an effective dose can initially be administered to a mammal, and the dose can then be gradually increased over time until the desired effect is achieved.

In another aspect, provided herein is a method of modulating endothelial function, where the method comprises or consist essentially of administering to a subject an effective amount of an inhibitor of TERT mitochondrial translocation, whereby administration of the inhibitor of TERT mitochondrial translocation modulates endothelial function in the subject.

The frequency and duration of administration can be any frequency or duration that improves a symptom of, for example, CED without being toxic. For example, an agent can be administered once or twice a day, once every other day, once or twice a week, or as needed. The frequency of administration can remain constant or can be variable during the duration of treatment. An effective duration of treatment can vary from several weeks to several months or years. For example, an effective duration of treatment can be six months, five years, or a lifetime. In addition, a course of treatment can include rest periods. Multiple factors can influence the actual effective frequency and duration of treatment. For example, the activities of the particular therapeutic agents used, the severity of the condition being treated, the doses administered, and the condition and prior medical history of the mammal being treated can affect the effective frequency and duration of treatment.

The compositions provided herein can be administered primarily orally, intravenously, parenterally, sublingually or transdermally. The corresponding drug preparation is preferably produced in liquid or solid form. Solutions are suitable for this purpose, especially for preparation of drops, injections or aerosol sprays, in addition to suspensions, emulsions, syrups, tablets, film tablets, coated tablets, capsules, pellets, powders, pastilles, implants, suppositories, creams, gels, salves, plasters or other transdermal systems.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

As used herein and in the appended claims, the singular forms "a", "an", and "the" include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods and pharmaceutical compositions described herein.

Unless defined otherwise, all technical and scientific terms used herein have the same meaning as commonly understood by one of ordinary skill in the art to which the invention belongs. Many variations of the present invention will suggest themselves to those skilled in the art in light of the above-detailed description. All such obvious modifications are within the full intended scope of the appended claims. This invention is further illustrated by the following examples which are to be regarded as illustrative only, and in no way limit the scope of the invention.

EXAMPLES

Overexpression of telomerase is associated with cardiac and vascular protection (Bar et al., 2014); however, re-activation of the telomerase enzyme in certain cell types may also be an important event in oncogenic transformation, given the role of telomerase in cellular immortalization and proliferation. The mechanisms that underlie the beneficial effects of telomerase reactivation in the prevention and amelioration of cardiac and vascular diseases have to this point been unclear. We report here the discovery that mitochondrial-associated telomerase and not nuclear telomerase is the cause of cardiovascular protection associated with telomerase activity. We have developed novel peptide therapeutics that are capable of specifically altering telomerase localization. Inhibition of nuclear transport of TERT, the catalytic subunit of telomerase, increases cytoplasmic (including mitochondrial) telomerase localization and more importantly, activity. This represents a strategy to harness the benefits of telomerase overexpression in cardiac and vascular disease without increasing cancer risk, and also provides an entirely new and novel means of inhibiting nuclear telomerase in cancer in a manner that is less toxic. In addition, these novel therapeutics could be combined with traditional and targeted cancer therapies to minimize toxicity to the vasculature and heart. Our data suggest that modulation of telomerase localization may be the basis of an entirely new way to treat microvessel, vascular and cardiac disease, including both chronic and acute conditions. Specifically, we show that increased mitochondrial translocation of TERT (by inhibiting nuclear translocation) has beneficial effects including prevention of Angiotensin II (ANG II)-induced endothelial dysfunction and oxidative stress, well-established predictors for a number of cardiovascular events.

Example 1—Use of Peptides to Modulate Telomerase Localization: Implications for Vascular Function & Disease Methods Decoy Peptide Development:

Decoy peptides encompassing the telomerase NLS were designed based on the characterization of the telomerase NLS previously performed (Chung et al., *Cell Sci*, 2012. 125 (Pt 11): p. 2684-97). Peptide sequences were designed based on the amino acid sequence of human telomerase (hTERT; UniProt 014746).

Peptides Synthesis and Handling:

Peptide synthesis was conducted by GeneMed Synthesis (San Antonio, Tex.). All peptide sequences were verified by mass spectrometry, and were only used at a purity of greater than 95%. Lyophilized peptides were stored at −20 degrees Celsius. Given the charge properties of the peptides used in these studies, phosphate buffered saline (PBS) was selected as the solvent of choice to dissolve all peptides used. Following dissolution of peptides in PBS, peptide aliquots (to minimize freeze/thaw cycles) were stored at −80 degrees Celsius. For experiments with labeled peptides, a 5-carboxyfluorescein tag was added to peptides (N-terminus) in a synthesis process conducted by GeneMed Synthesis. Specific peptide sequences are detailed below in Table 1.

TABLE 1

Sequences of Exemplary Peptide Inhibitors of Telomerase Localization to Nucleus or Mitochondria

| | nucXTERT |
|---|---|
| Wild-type (nucXTERT/ nucXTERT-W) | RRRGGSASRSLPLPKRPRR (SEQ ID NO: 1)** |

TABLE 1-continued

Sequences of Exemplary Peptide Inhibitors of Telomerase Localization to Nucleus or Mitochondria

| | |
|---|---|
| Phosphomimetic (nucXTERT-E) | RRRGGEASRSLPLPKRPRR (SEQ ID NO: 2) |
| Alanine substitution/ phosphodeficient (nucXTERT-A) | RRRGGAASRSLPLPKRPRR (SEQ ID NO: 3) |
| PEGylated variant with capped ends | Ac-CGGRRRGGEASRSLPLPKRPRR-peg12-amide (SEQ ID NO: 4) |
| MitoXTERT | |
| Wild-type | MPRAPRCRAVRSLLRSHYRE (SEQ ID NO: 5) |

**Bolded residue in SEQ ID NO: 1 represents position 227 of the telomerase enzyme, where a serine in the wild type sequence is phosphorylated to enable nuclear import of telomerase.

Microvessel Selection:

Microvessels were dissected from surgical discard tissues, predominantly consisting of adipose. Only vessels with a diameter of less than 300 micrometers were selected for further study. All microvessels were obtained from discarded surgical tissues, in accordance with an Institutional Review Board approved protocols (PRO00000114, PRO00010828, PRO00001094) at the Medical College of Wisconsin, Milwaukee, Wis.

After dissection, vessels were incubated overnight in complete endothelial cell media, supplemented with 5% fetal bovine serum (Lonza) with or without peptides as described. Following overnight incubation, peptides were washed out and vessels were cannulated and transferred to physiological salt solution. A video microscopy setup enabled monitoring of vessels in real time. Vessels were pre-constricted with endothelin-1 (ET-1) at a dose range of 0.1-1 nM. Only vessels capable of constricting at least 20% from baseline were included in the study. Flow-mediated dilation (FMD) and Ach-induced dilation were then evaluated, followed by evaluation of endothelium-independent dilation to papaverin. After establishing this baseline, vessels were pre-constricted again with ET-1 and dilator curves repeated in the presence of Angiotensin II (ANG II), as described below.

FMD was evaluated by adjusting the heights of two reservoirs in equal and opposite directions to generate flow by altering vessel central pressure. After each change in pressure gradient, vessel diameter was measured and assessed using video microscopy. Prior to measuring FMD, all vessels studied were pre-constricted using endothelin-1.

Dependence of vessels on NO versus hydrogen peroxide signaling in dilation was assessed using the pharmacologic agents Nw-nitro-L-arginine methyl ester (L-NAME; 100 µmol/L) and polyethylene glycol-catalase (PEG-catalase; 500 U/mL), respectively, where described.

ANG II Challenge:

Baseline vessel parameters, including ability to dilate in response to FMD, as described above were assessed. Following assessment, vessels were treated with ANG II at a final concentration of 10 nM for 30 minutes before FMD and response to ACh was re-assessed.

Cell Culture:

The NCI-H1299 cell line was used for the cell culture experiments described in this manuscript. Cells were cultured in RPMI (Invitrogen) supplemented with 10% fetal bovine serum (Sigma).

Cell Fractionation:

Treated H1299 cells were fractionated into a nuclear and non-nuclear component using the NE-PER Nuclear and Cytoplasmic Extraction reagent kit (Thermo Fisher).

ddPCR TRAP Assay:

Cell lysates from H1299 cells treated overnight with nucXTERT peptides were obtained and fractionated, in accordance with the protocol established in the Thermo-Fisher NE:Per kit, resulting in a nuclear and non-nuclear fraction. A modified, quantitative telomerase repeat amplification protocol (TRAP assay) was performed. Briefly, 2 micrograms of lysate from the nuclear fraction and 4 micrograms of protein lysate from the non-nuclear fraction isolated with the ThermoFisher NE:Per protocol were incubated with the previously described TS oligo nucleotide, and elongation of the product was allowed to occur with slight modification to the original procedure described by Kim et al. Following generation of repeats, samples were subjected to droplet generation using the QX200 (BioRad) Droplet generator which uses an oil:water emulsion to produce individual droplets for analysis. PCR was then performed on the samples using a standard thermal cycler, and conditions outlined by Kim et al. Following PCR, samples were loaded into the QX200 Droplet Reader and droplets were sampled to determine the percentage of positive droplets present in each individual sample.

Western Blot:

Protein lysates were prepared following fractionation of H1299 cells into the nuclear and non-nuclear compartment, as described above. Following fractionation, protein within each sample was quantified using a BCA assay. 30 µg of protein was obtained from each fraction. Lysates were boiled and denatured. Samples, complete with loading dye were loaded into a 4-12% Bis-Tris gel. A current of 110V was applied for 75 minutes to separate proteins by size. Proteins were then transferred to a PVDF membrane (BioRad) for 2 hours at 100 V, over ice and with cooling. Following transfer, membranes were blocked with 10% powdered blocking reagent (BioRad) dissolved in Tween-20 Tris-Buffered Saline (TBST) for 2 hours at room temperature. Following blocking, membranes were incubated with primary antibody (anti-hTERT (rabbit), Rockland, 1:500; anti-GAPDH (rabbit), Cell Signaling Technology, 1:1,000; anti-Histone H3, Cell Signaling Technology, 1:1,000) dissolved in 5% blocking agent TBST overnight at 4 degrees Celsius. Following overnight incubation, membranes were washed thoroughly with TBST and incubated with anti-rabbit antibody (Cell Signaling Technologies) at a 1:5000 dilution for 2 hours. Following thorough washing, membranes were incubated with Femto detection solution (hTERT; Histone H3) or BioRad ECL solution (GAPDH). Membranes were then imaged using an ECL detection system (BioRad).

Figure 2A:
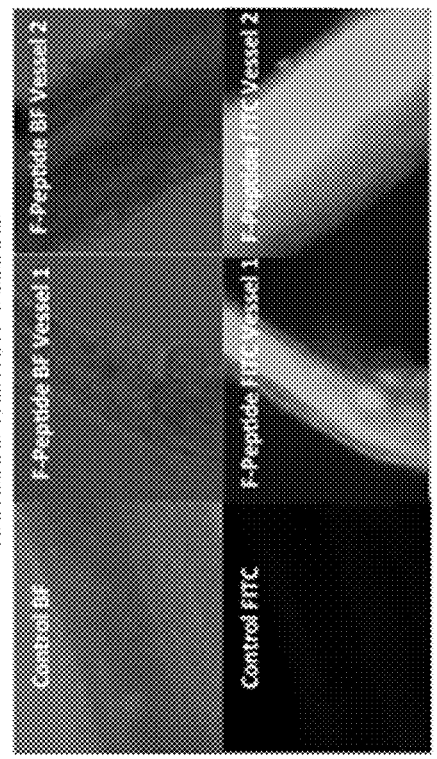
FIGS. 2A-2B. (A) Dissected human microvessels are shown. The top panels are brightfield images, while the bottom three panels are images of the same vessels under laser excitation with a filter to visualize emission from 5-FAM. Vessels were treated with 5-FAM labeled peptide (nucXTERT-W) at a 10 uM concentration for 8 hours (h), or left untreated (control). (B) H1299 non-small cell lung carcinoma cells were seeded onto slides and treated with 0, 50, or 100 µM 5-FAM labeled nucXTERT-W for 8 h. DAPI=blue; 5-FAM labeled peptide=green.
Figure 2B:
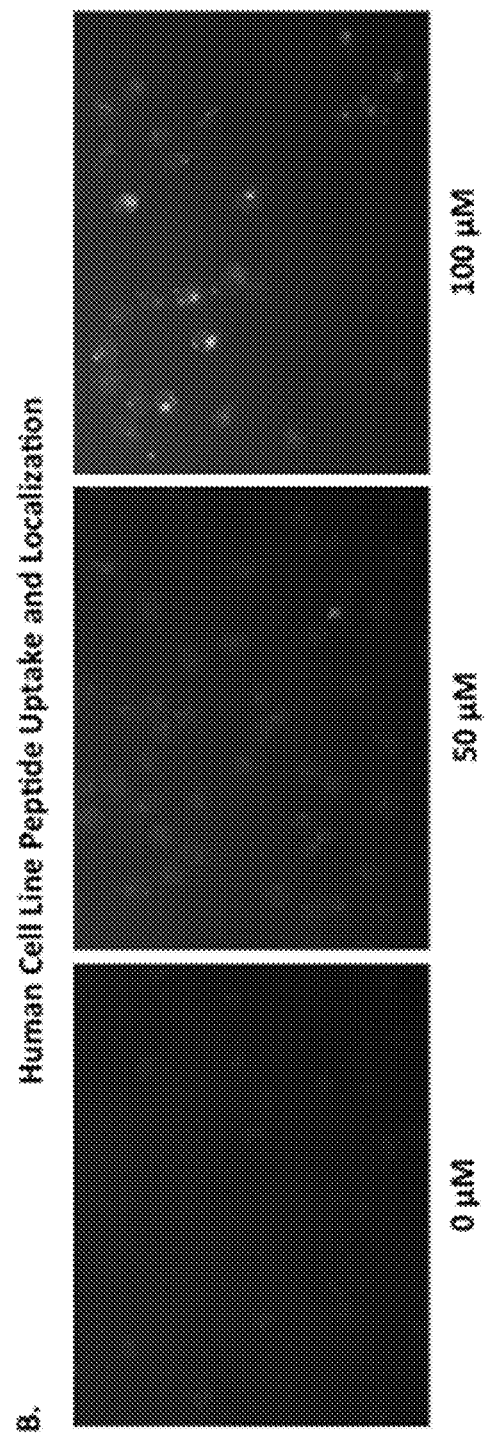

Results nucXTERT Inhibitor is Effectively Taken Up by Living Tissues:

One of the first hurdles that required consideration when evaluating the ability of novel peptides to alter telomerase localization is their ability to be internalized by living tissues. nucXTERT was labeled with 5-carboxyfluorescein (5-FAM). Isolated human microvessels incubated with the 5-FAM labeled peptide were analyzed by microscopy. Robust signal is present in vessels pulsed with the peptide, while vessels not treated with peptide have no signal. Similarly, in vitro experiments using human non-small cell lung cancer (H1299) cells confirm that labeled peptide effectively traffics into the cell. In addition, the peptide is detectable in a perinuclear pattern (FIG. 2). Since peptide is taken up by vessels, it was possible to study the effect of peptide treatment on vessel physiology, using human microvessels as described in the methods. Table 2 details the patient characteristics from whom microvessels were isolated for the remainder of the experiments conducted in this chapter.

TABLE 2

Patient Characteristics

| Characteristics | Non-CAD (n = 29) | CAD (n = 4) |
|---|---|---|
| Sex (M/F) | 7/21 | 2/2 |
| Age | 47.78 ± 10.39 | 72 ± 9.27 |
| BMI | 29.90 ± 5.41 | 33.1 ± 6.87 |
| BMI ≥30 | 13 out of 28 | 1 out of 4 |
| Risk Factors | | |
| Coronary Artery Disease | 0 | 4 |
| Hypertension | 3 | 1 |
| Hypercholesterolemia | 1 | 1 |
| Diabetes Mellitus | 0 | 1 |
| Congestive Heart Failure | 0 | 0 |
| No Risk Factors | 25 | 0 |

Figures 3A, 3B:
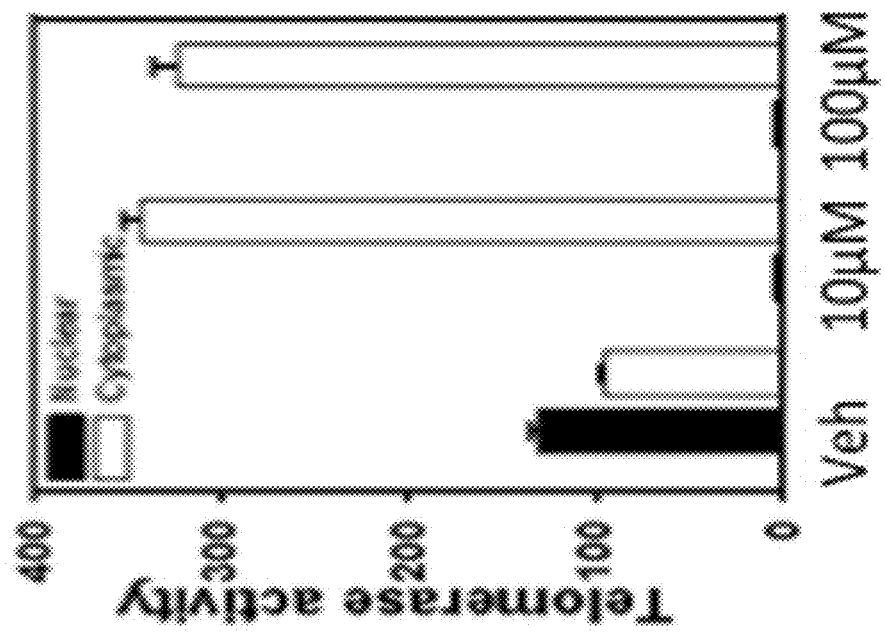
FIGS. 3A-3B. (A) Western blotting with using H1299 cells fractionated into nuclear and cytosolic compartments after overnight treatment with nucXTERT-W at the indicated doses. GAPDH serves as a cytoplasmic loading control, while histone H3 serves as a nuclear loading control. (B) Densitometry quantification of Western blots presented in A expressed as a ratio of nuclear:cytoplasmic signal after normalization to nuclear and cytoplasmic loading controls, respectively.
Figures 4A, 4B:
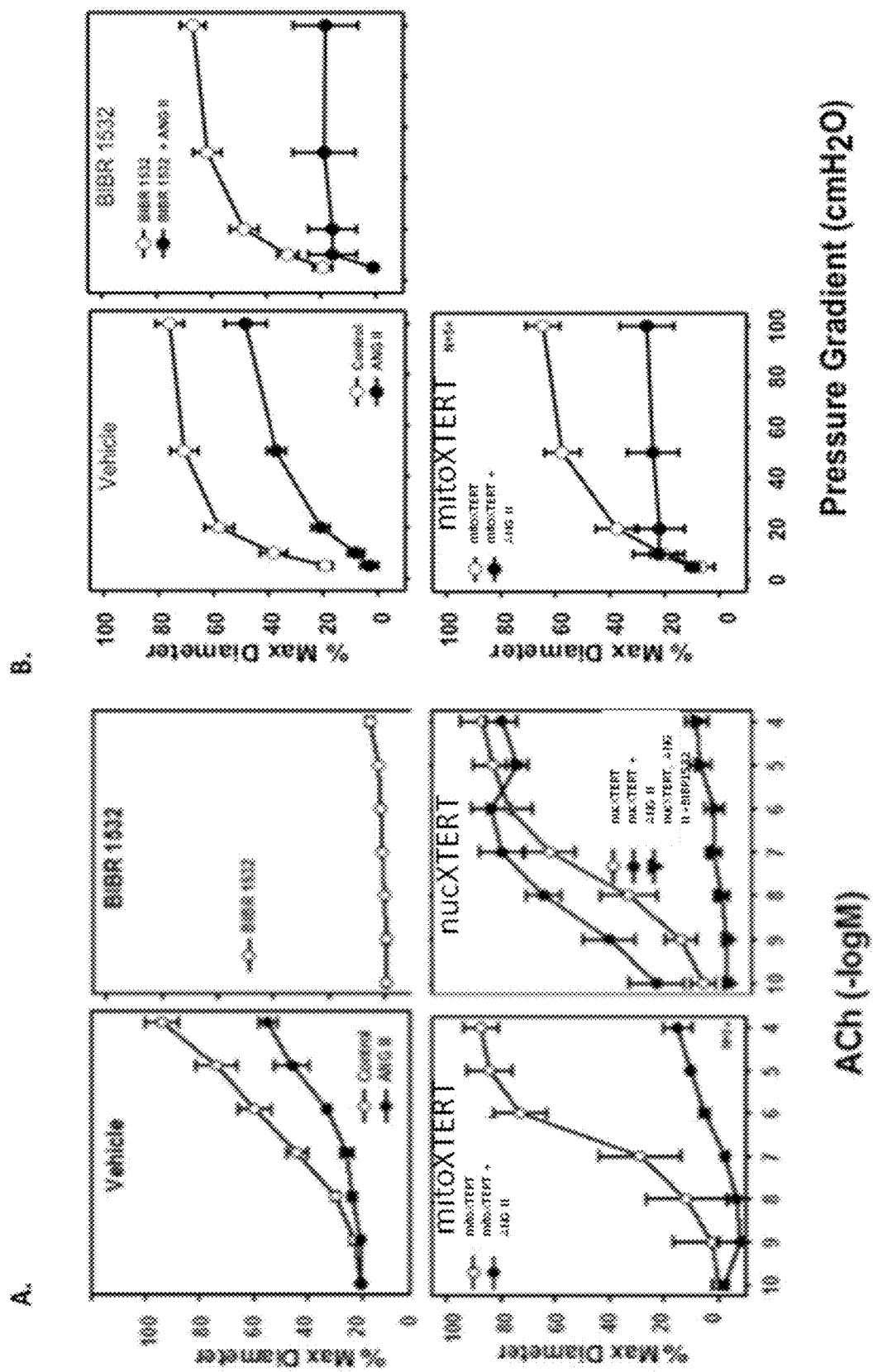
FIGS. 4A-4B demonstrate that nucXTERT peptide protects human vessels from stressors. (A) Live human microvessels were dissected from adipose of healthy donors and treated overnight with either BIBR1532 (telomerase inhibitor), mitoXTERT, or nucXTERT (and nucXTERT+ BIBR1532). Vessels were then challenged with acetylcholine (ACh) dilation stimulus with or without ANG II stressor. (B) Human microvessels prepared as in A were treated overnight with BIBR1532, mitoXTERT or nucXTERT (and nucXTERT+BIBR1532). Vessels were then challenged with a pressure gradient dilation stimulus with or without ANG II.

**All microvessels isolated from adipose samples;
***Patient characteristics not available for one NON-CAD vessel used nucXTERT Inhibitor Alters Telomerase Localization:

Telomerase activity assays as well as western blotting, depicted in FIGS. 3A-3B, reveal that H1299 cells pulsed with nucXTERT peptide have attenuated nuclear levels of telomerase. This is reflected in decreased telomerase activity, as measured by TRAP assay (FIG. 3B). Furthermore, treatment with nucXTERT increases accumulation of telomerase within the non-nuclear compartment.

nucXTERT Protects Human Microvessels from Stressors:

Isolated human microvessels were pretreated with nucXTERT and challenged with angiotensin II (ANG II), a potent vasoconstrictor and vascular stressor involved in several disease pathologies (obesity, hypertension, renal failure, CAD to name a few). Vasodilation was evoked using increased intralumuinal flow (flow mediated dilation or "FMD") or the endothelium-dependent agonist acetylcholine (ACh). Smooth muscle-dependent and endothelial cell-independent dilation was tested using papaverin. Treatment of microvessels with ANG II results in significantly diminished vasodilator responses to both acetylcholine and flow as measured by the percentage of maximum diameter. Treatment of microvessels with BIBR1532, a known specific inhibitor of global telomerase activity (Pascolo et al., *J Biol Chem*, 2002) effectively eliminates vasodilation in response to acetylcholine (FIG. 4A, upper right), although vessels continue to dilate in response to flow stimulus (FIG. 4B, upper right). When vessels are pre-treated with nucXTERT, vasodilation in response to either ACh or flow stimuli is not impacted by ANG II treatment. However, treatment with nucXTERT and BIBR1532 effectively abrogates the vasodilator protective effect of nucXTERT, suggesting that catalytic telomerase activity is required in order for nucXTERT to preserve baseline vasodilation in response to ANG II challenge.

Interestingly, when vessels are pre-treated with mitoXTERT inhibitor, a decoy peptide containing regions of the telomerase MLS, no protection of the endothelium from ANG II stress with either flow or ACh stimulus is observed. We hypothesize that this is due to an ability of this peptide to compete with telomerase for import into the mitochondria; however, additional work, including mitochondrial fractionation and Western blotting for telomerase expression is required to illustrate whether or not mitoXTERT is capable of influencing mitochondrial accumulation of telomerase protein (FIGS. 4A-4B, bottom left panels).

Accordingly, our in vivo and ex vivo data demonstrate that nucXTERT and mitoXTERT peptides antagonize the adverse cardiac effects of angiotensin II (ANG II), which causes significant cardiac and vascular damage and is associated with hypertension and many other CV disease states.

nucXTERT Modified Peptides Differentially Protect Vasculature:

It was not previously known or demonstrated that global inhibition of TERT activity increases sensitivity to stress induced endothelial dysfunction and has negative effects on cardiovascular outcomes, but specific inhibition of nuclear TERT localization and nuclear activity has protective effects on vasculature by maintaining mitochondrial TERT function. As described in this section, it was discovered that treatment of isolated human vessels with TERT peptide inhibitors attenuated vessel responses to stressors including ANG II in a manner that is suggestive that the peptide inhibitor may protect the vasculature from damage resulting from a number of chronic pathologies, oxidative stressors and chemotherapies associated with vascular and cardiac toxicities.

Figures 5A, 5B, 5C:
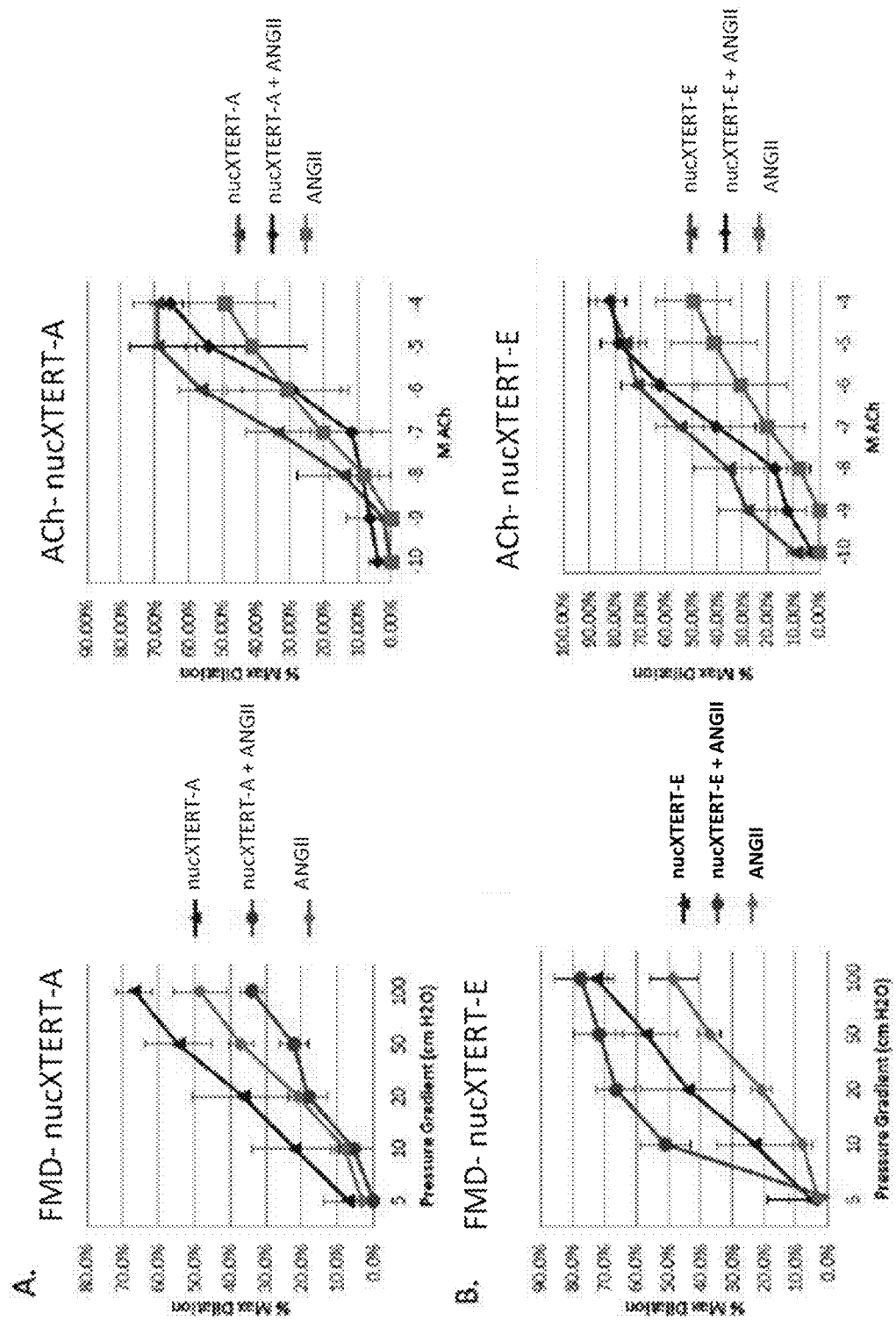
FIGS. 5A-5C. (A) nucXTERT-A (sequence detailed in C) was used to treat human microvessels overnight. Flow and ACh were then used as dilation stimuli with or without ANG II. (B) nucXTERT-E (sequence detailed in C) was used to treat human microvessels overnight. Flow and ACh were then used as dilation stimuli with or without ANG II. (C) Table detailing the sequences and effectiveness of various nucXTERT variants tested.
Figure 6:
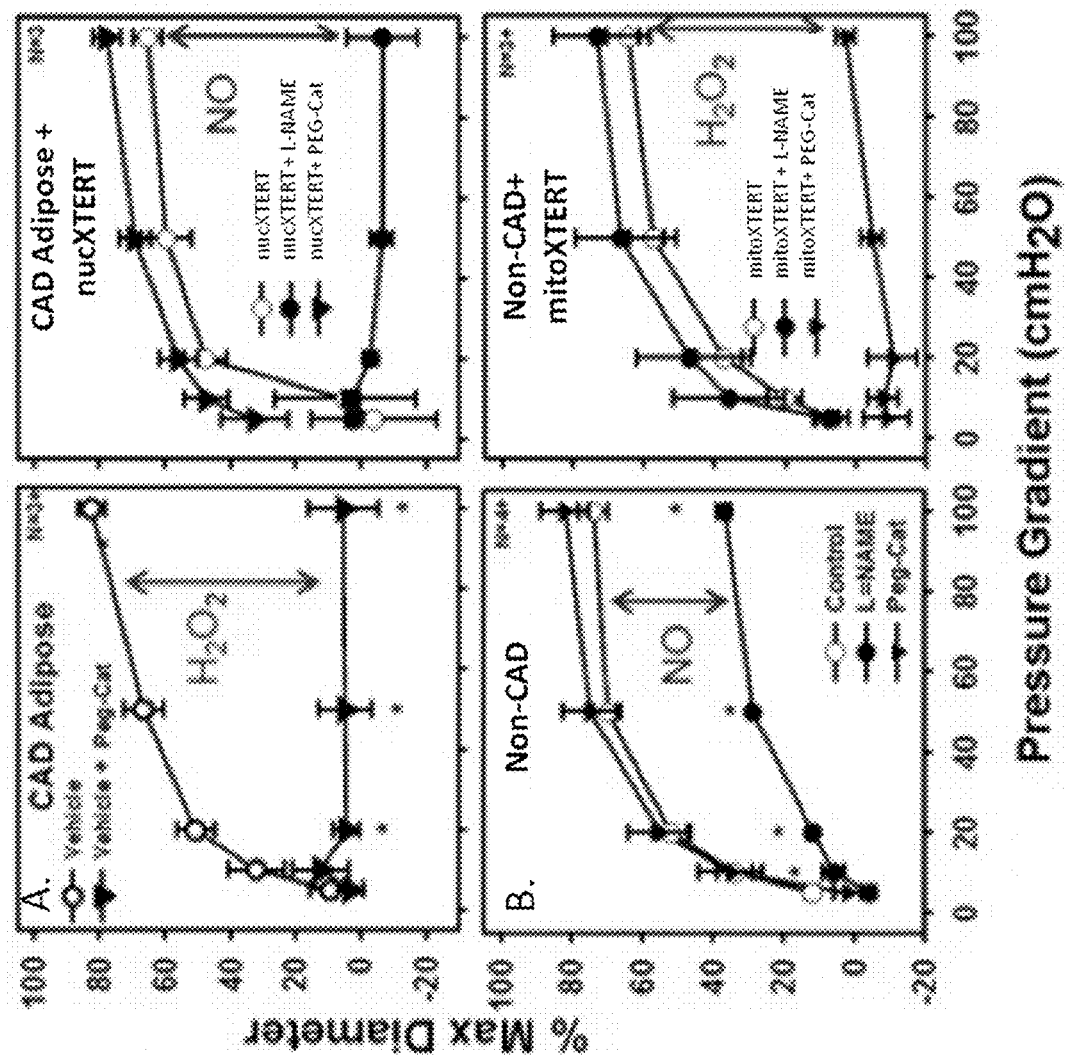
FIG. 6 demonstrates that nucXTERT peptide restores function of coronary artery disease human microvessels. Live human microvessels were dissected from adipose from individuals with clinically confirmed coronary artery disease (CAD). Vessels were treated with nucXTERT in the presence of either vehicle or L-NAME or PEG-Catalase. Response to pressure gradient (flow) stimulus was evaluated. Microvessels from the adipose of healthy human donors was treated with either vehicle or mitoXTERT with or without NG-nitro-L-arginine methyl ester (L-NAME) or PEG-Catalase. The ability of the vessels to dilate in response to a pressure gradient (flow) was assessed.

Post-translational modifications play a key role in cellular trafficking of regulated proteins. Wild type nucXTERT is a synthetic peptide homologous to one of the nuclear localization signals present in telomerase. The serine residue at position 227 can be phosphorylated to initiate nuclear translocation of the protein. We synthesized several variants based on this primary sequence, including a phosphomimetic containing a glutamic acid substitution at position 227 (nucXTERT-E), as well as a non-phosphorylatable substitution mutant having an alanine at position 227 of the telomerase enzyme-encoding sequence (nucXTERT-A; see peptide sequences detailed in Table 1). Interestingly, nucXTERT-A does not protect vessels from attenuation of vasodilator capacity in response to AngII challenge with either flow or acetylcholine (ACh) dilation stimuli (FIG. 5). Vessels incubated with the A peptide at a concentration of 10 μM overnight had a mean diameter of 142 μm±38. Vessels incubated with the E peptide had a mean diameter of 145 μm±49. Baseline vessel constriction was similar between both A and E peptide treated vessels, with A treated vessels constricting to an average of 53±12% of their maximum diameter after 10 minutes of ET-1 treatment, while E peptide treated vessels constricted to an average of 48±18% of their maximum diameter after 10 minutes of ET-1 treatment. After treatment with ANG II and stimulation by a flow gradient, A peptide treated vessels dilated to a diameter of 82 μm±11 at a 100 cm flow gradient. By contrast, E peptide treated vessels dilated to an average diameter of 136 μm±51 at 100 cm of flow gradient, following ANG II treatment (FIGS. 5A and 5B, right hand panels). When A peptide treated vessels were exposed to ANG II and stimulated with ACh, vessels dilated to an average diameter of 128 μm±33. E peptide treated vessels treated with ANG II and stimulated with ACh dilated to an average diameter of 131 μm±24. The phosphomimetic nucXTERT referred to herein as nucXTERT-E prevents ANG II-induced endothelial dysfunction in isolated microvessels under both flow and ACh stimulus conditions, at a level which is indistinguishable from treatment with the wild type sequence.

nucXTERT Inhibitor Restores Healthy Vasodilatory Mechanisms in Diseased Tissues:

Diseased microvessels exhibiting vascular dysfunction were obtained from adipose tissue of donors with clinically confirmed coronary artery disease. At baseline, these vessels respond to vasodilatory stimuli through the use of H2O2 as a signaling mechanism to enable dilation. Treatment of vessels with PEG-Catalase, a scavenger of H2O2 effectively attenuates vasodilation. However, treatment with L-NAME, an inhibitor of nitric oxide synthase does not impact the ability of diseased vessels to dilate. By contrast, vessels from healthy donors exhibit the opposite trend; treatment with PEG-Catalase does not impact dilation potential, while treatment with L-NAME significantly attenuates the ability of the vessels flow stimuli. In vessels from subjects with CAD, $H_2O_2$ represents the dominant vasodilator. In vessels pretreated with nucXTERT, NO is restored as the main mechanism of FMD. In addition, treatment with PEG-Catalase no longer inhibits dilation responses (FIG. 6, top panels). In marked contrast, treatment with mitoXTERT causes healthy vessels to undergo the converse change, from NO-mediated dilation to $H_2O_2$-dependent dilation (FIG. 6, bottom panels).

Figures 7A, 7B, 7C:
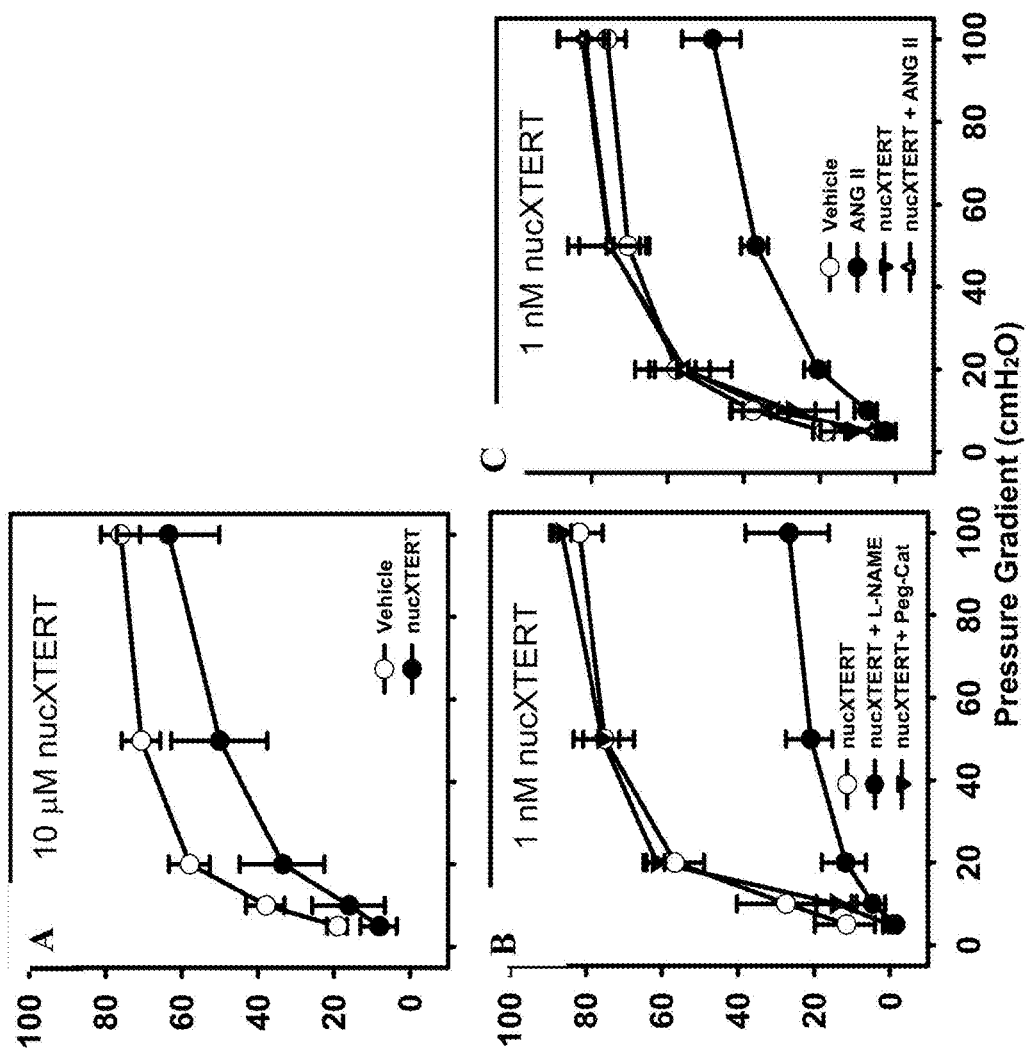
FIGS. 7A-7C show dose titration of PEGylated nucXTERT-E in isolated vessel studies. nucXTERT with S→E substitution was PEGylated at the C-terminus to increase bio stability and cell permeability. Effective doses from 10 µM to 1 nM were tested. PEGylated peptide could be titrated down to 1 nM with vascular protective effects. The mechanism of flow-mediated dilation (FMD) was not altered when non-CAD vessels were treated, remaining nitric oxide (NO) mediated (L-NAME inhibitable, B) but protected against ANG II induced endothelial dysfunction (C). N=3-4.

Dose titration of PEGylated nucXTERT E in Isolated vessel studies:

nucXTERT with S→E substituton was PEGylated at the C-terminus to increase bio stability and cell permeability. Effective doses from 10 μM to 1 nM were tested (FIGS. 7A-7C). PEGylated peptide could be titrated down to 1 nM with vascular protective effects. The mechanism of FMD did not alter (L-NAME inhibitable, FIG. 7B) but protected against ANG II induced endothelial dysfunction (FIG. 7C).

Figures 8A, 8B, 8C, 8D, 8E, 8F, 8G, 8H, 8I, 8J, 8K, 8L:
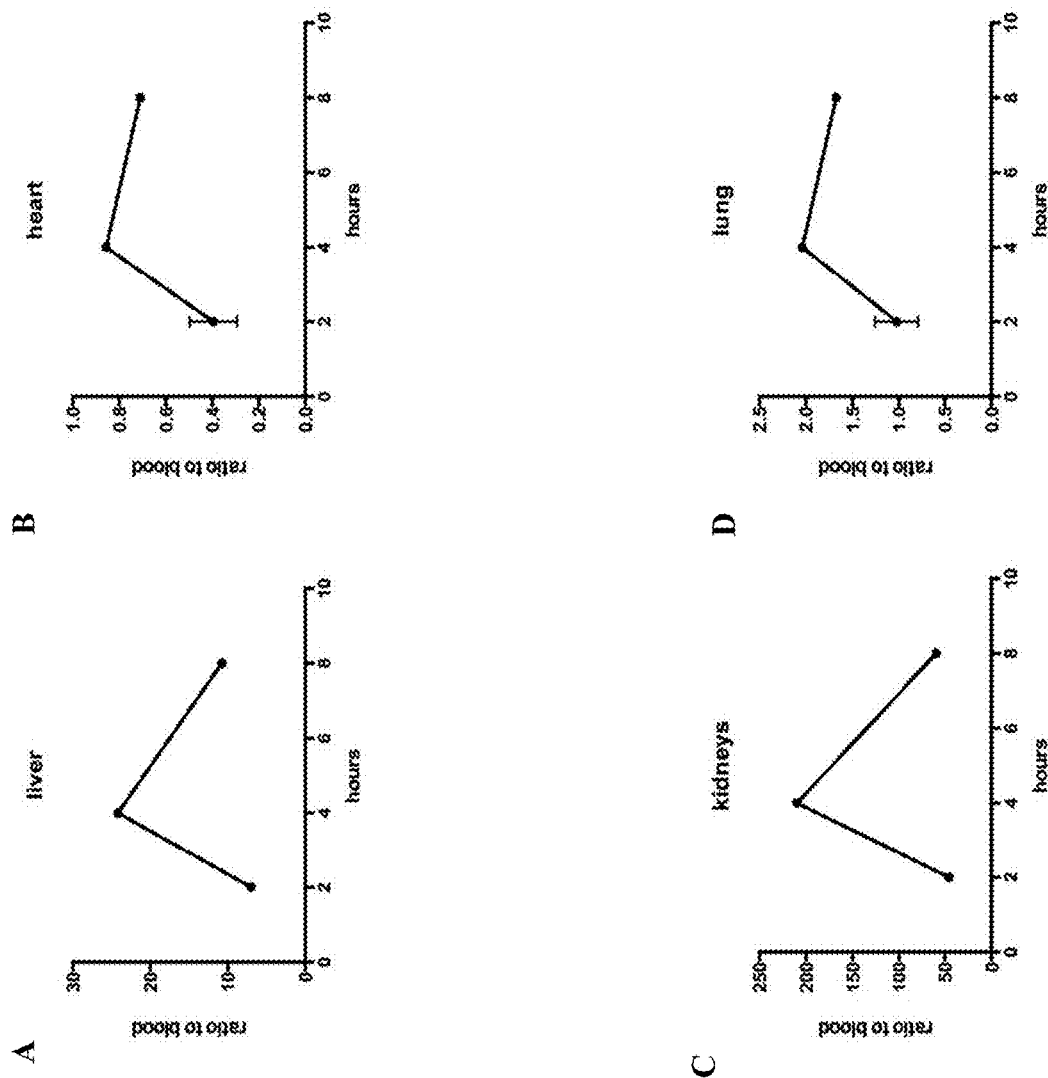
FIGS. 8A-8L show peptide biodistribution in vivo. PEGylated peptide (50 nM) was radiolabeled with *Technetium* (Tc 99m) for radiotracing. *Technetium* labeled peptide (0.77 nM) was injected into the tail vein of normal C57 mice. (A-K) Mice were euthanized at 2, 4, and 8 hours after injection and remaining radioactivity determined in individual organs. Signals were normalized to blood. In every major organ significant increase of signal was observed up to 8 hours after injection, suggesting the peptide was not degraded at this time. (L) Mice were injected subcutaneously (subQ) with radiolabeled peptide (0.77 nM) and remaining activity determined in blood after 24 and 48 hours. N=5-6.

Peptide Biodistribution In Vivo:

To assay peptide biodistribution in vivo, pegylated peptide (50 nM) was radiolabeled with *Technetium* (Tc 99m) for radiotracing. *Technetium*-labeled peptide (0.77 nM) was injected into the tail vein of normal C57 mice. For FIGS. 8A-8K, mice were euthanized at 2, 4, and 8 hours after injection and remaining radioactivity determined in individual organs. Signals were normalized to blood. In every major organ significant increase of signal was observed up to 8 hours after injection, suggesting the peptide was not degraded at this time. In FIG. 8L, mice were injected subcutaneously (subQ) with radiolabeled peptide (0.77 nM) and remaining activity was determined in blood after 24 hours and 48 hours. While signal was significantly lower in subQ mice as compared to IV injection, increased signal relative to background was observed after 24 hours but not 48 hours. These data suggest the peptide is distributed in the circulation for at least 24 hours after subQ injection. As the peptide is positively charged, our data demonstrate that the peptide crosses the blood brain barrier—an advantageous property of the peptides provided herein that could prove important to the treatment of cerebral vascular dysfunction or neurological disorders. Peptides having bioactivity in the CNS in vivo open up a realm of possible therapeutic options for neurologic diseases cerebral vascular disorders.

Figure 9:
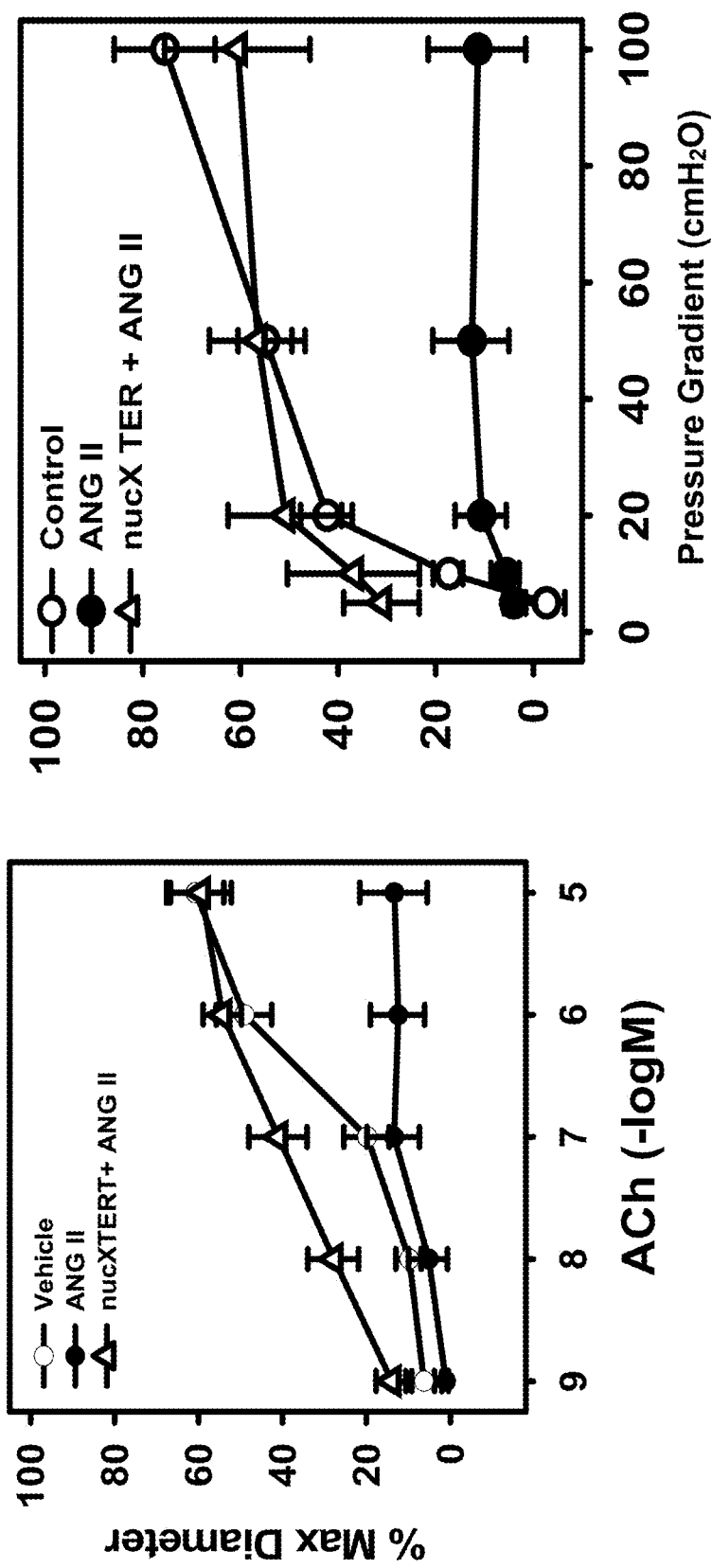
FIG. 9 demonstrates in vivo effects of Peg-nucXTERT. Mice were treated with commonly used stressors to induce hypertension and endothelial dysfunction. The fast pressor dose of ANG II (1000 ng/kg/min) was infused via osmotic mini-pump for 14 days. A subgroup of animals was co-treated with nucXTERT (30 µg/day via osmotic mini-pump) in addition to ANG II, for the same duration and using the same delivery system. Curves were compared to historic controls (vehicle). ANG II caused a significant decrease to agonist induced endothelium-dependent dilation (ACh, A) or FMD (B), while co-treatment with nucXTERT prevented onset of ANG II induced endothelial dysfunction. Smooth muscle-dependent dilation in response to vasodilator papaverin was not effected (data not shown). * P<0.05 vs. Vehicle one way ANOVA RM, N=5).

In Vivo Effects of Peg-nucXTERT:

To test in vivo effects of nucXTERT mice were treated with commonly used stress to induce hypertension and endothelial dysfunction. The fast pressor dose of ANG II (1000 ng/kg/min) was infused via osmotic minipump for 14 days. A subgroup of animals was co-treated with nucXTERT (30 μg/day via osmotic mini pump) in addition to ANG II, for the same duration and using the same delivery system. Curves were compared to historic controls (vehicle). As shown in FIG. 9, ANG II caused a significant decrease to agonist induced endothelial dependent dilation (ACh) or FMD. Co-treatment with nucXTERT prevented onset of ANG II induced endothelial dysfunction. Smooth muscle dependent dilation to papaverin was not effected (data not shown).

Discussion

We demonstrate that our synthetic nuclear telomerase inhibitor (nucXTERT) peptide is readily taken up by live human microvessels. Furthermore, in vitro experiments demonstrate that peptide uptake occurs in cultured human cell lines and that the peptide, as expected, localizes to the perinuclear region (FIG. 2). Western blotting and analysis of telomerase activity using a modified TRAP assay employing digital droplet PCR (ddPCR) revealed that treatment with nucXTERT dramatically decreases nuclear telomerase accumulation and activity, with corresponding increases in cytoplasmic accumulation and activity (FIG. 3).

Interestingly, treatment of isolated human microvessels dissected from adipose tissue of healthy patients are protected from vascular stressors by nucXTERT treatment (FIG. 4). Use of a modified nucXTERT peptide containing a glutamic acid for serine substitution at position 227 of the endogenous NLS also reveals striking vasoprotective effects. However, substitution of serine with alanine at the same position abrogates the effectiveness of nucXTERT, suggesting that this is a critical residue for the function of this peptide, and that our synthetic modification of the peptide may enhance function (FIG. 5). We also establish that nucXTERT is capable of altering the mechanisms responsible for vasodilation in tissues from patients with coronary artery disease. Treatment with nucXTERT restores vascular dilation to primarily nitric oxide (NO)-dependent mechanisms, as seen in healthy microvessels. Conversely, treatment with mitoXTERT, which is a peptide corresponding to the mitochondrial localization sequence (MLS) of telomerase, causes healthy tissues that are normally dependent on NO mediated dilation to become dependent on hydrogen peroxide to dilate in response to flow (FIG. 6).

Pre-treatment of vessels with global telomerase activators reveals that telomerase activity has a protective effect on the ability of the vasculature to resist stressors. This point has also been dramatically proved in vivo in models of cardiac injury and myocardial infarction, where overexpression of telomerase using AAV-vectors leads to significantly better recovery and lower mortality post-MI in a rodent model (Bar et al, 2014). Given data suggesting that telomerase can modulate the mechanism of vasodilation, the question or where the enzyme is acting is highly salient. We have demonstrated here that using decoy peptides, the telomerase pool can be effectively manipulated. Specifically, shifting telomerase to a predominantly non-nuclear localization also results in vasoprotection. Intriguingly, this vasoprotective effect is abolished when the catalytic activity of telomerase is inhibited. This suggests that the vasoprotective phenotype is dependent on telomerase activity, and that the inhibitor is specifically manipulating telomerase. The development of several different peptides further reveals the specificity of action of nucXTERT; mutation at one residue effectively prevents the peptide from protecting the vasculature. This strongly suggests that this is a highly specific therapeutic; the protective effect observed ex vivo is not due to treatment of tissues with peptide non-specifically—rather, this particular peptide is specific.

Most strikingly, shifting the localization of telomerase is capable of restoring normal vasodilator potential and normal mechanisms of vasodilation (NO mediated versus hydrogen peroxide) in freshly isolated human microvessels from patients with coronary artery disease. This immediately suggests the utility of this approach and these therapeutics in correcting vascular dysfunction associated with this disease state in this patient population. Furthermore, it suggests the utility of this approach in treating other cardiac and vascular diseases that involve microvessel dysfunction, including but not limited to CAD, Prinzmetal's angina and others.

To date, there are few effective therapies available to address underlying vascular dysfunction, which is an essential component of most cardiovascular disease. We provide a new approach and several new compounds that could be useful in the treatment of acute and chronic coronary, cardiac and vascular diseases. While the broad use of compounds that increase telomerase levels globally may draw concern given the potential to accelerate or enable cellular transformation, these peptides present significantly less oncogenic risk. Inhibition of nuclear telomerase activity that occurs when nucXTERT peptides are used could also be used as a treatment in cancer. In fact, a recent strategy that activated the natural inhibitor pathway of nuclear telomerase activity has successfully shown that this approach increases cancer sensitivity to chemotherapeutic agents by inhibiting initiation of autophagy. Already, telomerase inhibitors that are in clinical trials have demonstrated anti-tumor efficacy. However, inhibition of the catalytic activity of the telomerase enzyme on a global level, much as demonstrated by BIBR1532 is likely to cause serious vascular compromise. These therapies may increase endothelial dysfunction and increase risks such as thrombosis. This is particularly troubling given the length of time that patients may need to take anti-telomerase regimens in order to see activity against tumors. Attempting to re-mobilize the endogenous telomerase pool to prevent telomere elongation (nuclear activity) that is required for tumor cell proliferation could inhibit tumor cell proliferation while also significantly lowering the risk of endothelial damage or thrombotic events by preserving telomerase function at the mitochondria in endothelium. Many existing anti-cancer therapies also indirectly inhibit telomerase activity, resulting in vascular damage and increased risk of thrombosis. nucXTERT peptides could help to address these toxicities by shifting the nuclear pool of telomerase to protect endothelial cell health.

A number of additional studies should be undertaken to verify that telomerase does in fact localize not just to the cytoplasmic pool, but more specifically to the mitochondrial compartment following treatment with nucXTERT. Additionally, experiments to confirm altered telomerase localization after treatment with the phosphomimetic peptide (nucXTERT-E) as well as following treatment with the phosphorylation-deficient peptide (nucXTERT-A) should be conducted. These experiments would involve fractionation of treated cells and potentially vessels with subsequent Western blotting and TRAP assay experiments to validate both increase protein levels and activity within the mitochondrial compartment.

Example 2—NLS Peptide Inhibitor May Decrease Lung Tumor Cell Migration

Recent publications have shown short term cardiac protective effects of increased telomerase activity (Bar et al.) and indirect activation of the natural inhibition of nuclear telomerase activity inhibits activation of cellular autophagy—one of the key contributors to chemotherapy resistance of tumors. Our data suggest that the peptide inhibitor may decrease the migratory potential of a highly invasive and metastatic lung tumor cell line.

The following list of references are incorporated herein in their entirety by reference:

Bar, C., et al., *Telomerase expression confers cardioprotection in the adult mouse heart after acute myocardial infarction.* Nat Commun, 2014. 5: p. 5863.

Widlansky, M. E., et al., *The clinical implications of endothelial dysfunction.* J Am Coll Cardiol, 2003. 42(7): p. 1149-60.

Freed, J. K., et al., *Ceramide changes the mediator of flow-induced vasodilation from nitric oxide to hydrogen peroxide in the human microcirculation.* Circulation research, 2014. 115(5): p. 525-532.

Beyer, A. M., et al., *An Acute Rise in Intraluminal Pressure Shifts the Mediator of Flow Mediated Dilation from Nitric Oxide to Hydrogen Peroxide in Human Arterioles.* American Journal of Physiology-Heart and Circulatory Physiology, 2014: p. ajpheart. 00557.2014.

Kothawade, K. and C. N. Bairey Merz, *Microvascular coronary dysfunction in women: pathophysiology, diagnosis, and management.* Curr Probl Cardiol, 2011. 36(8): p. 291-318.

Leeansyah, E., et al., *Inhibition of telomerase activity by human immunodeficiency virus (HIV) nucleos (t) ide reverse transcriptase inhibitors: a potential factor contributing to HIV-associated accelerated aging.* Journal of Infectious Diseases, 2013: p. jit006.

Eitan, E., et al., *Novel telomerase-increasing compound in mouse brain delays the onset of amyotrophic lateral sclerosis.* EMBO Mol Med, 2012. 4(4): p. 313-29.

Spilsbury, A., et al., *The role of telomerase protein TERT in Alzheimer's disease and in tau-related pathology in vitro.* J Neurosci, 2015. 35(4): p. 1659-74.

Mouraret, N., et al., *Role for telomerase in pulmonary hypertension.* Circulation, 2015. 131(8): p. 742-55.

Asai, A., et al., *A novel telomerase template antagonist (GRN163) as a potential anticancer agent.* Cancer Res, 2003. 63(14): p. 3931-9.

Santos, J., D. Gutterman, and A. Beyer, *Mitochondrial telomerase regulates flow mediated dilation by suppressing mitochondrial derived free radical production (664.1).* The FASEB Journal, 2014. 28 (1 Supplement): p. 664.1.

Hockenberry, J., D. D. Gutterman, and A. M. Beyer, *Overexpression of the Catalytic Subunit of Telomerase Protects Against Ang II Induced Vascular Dysfunction.* Hypertension, 2014. 64 (Suppl 1): p. A538-A538.

Chung, J., P. Khadka, and I. K. Chung, *Nuclear import of hTERT requires a bipartite nuclear localization signal and Akt-mediated phosphorylation.* J Cell Sci, 2012. 125 (Pt 11): p. 2684-97.

Santos, J. H., et al., *Mitochondrial hTERT exacerbates free-radical-mediated mtDNA damage.* Aging Cell, 2004. 3(6): p. 399-411.

Pascolo, E., et al., *Mechanism of human telomerase inhibition by BIBR1532, a synthetic, non-nucleosidic drug candidate.* J Biol Chem, 2002. 277(18): p. 15566-72.

Jeong, S. A., et al., *Akt-mediated phosphorylation increases the binding affinity of hTERT for importin a to promote nuclear translocation.* J. Cell Sci., 2015: p. jcs. 166132.

Kim, N. W., et al., *Specific association of human telomerase activity with immortal cells and cancer.* Science, 1994. 266(5193): p. 2011-5.

Mender, I. and J. W. Shay, *Telomerase Repeated Amplification Protocol (TRAP).* Bio Protoc, 2015. 5(22).

The present invention has been described in terms of one or more preferred embodiments, and it should be appreciated that many equivalents, alternatives, variations, and modifications, aside from those expressly stated, are possible and within the scope of the invention.

We claim:

1. An isolated peptide comprising a phosphomimetic residue, the peptide comprising the amino acid sequence of SEQ ID NO:6 (RRRGGX$_1$ASRSLPLPKRPRR);
   wherein X$_1$ is the phosphomimetic amino acid residue selected from the group consisting of aspartic acid and glutamic acid, and wherein the isolated peptide is no more than 22 amino acids in length.

2. The isolated peptide of claim 1, as set forth by SEQ ID NO:2.

3. The isolated peptide of claim 1, wherein the peptide is blood brain barrier (BBB)-permeant.

4. The isolated peptide of claim 1, wherein the peptide is PEGylated.

5. The isolated peptide of claim 4, wherein the PEGylated peptide comprises the sequence set forth in SEQ ID NO:4.

6. The isolated peptide of claim 1, further comprising one or more modifications selected from PEGylation, myristoylation, glycosylation, acetylation, phosphorylation, and addition of a linker or spacer.

7. The isolated peptide of claim 1, wherein the peptide is an inverso or retro-inverso peptide.

8. An isolated polynucleotide comprising a nucleic acid sequence encoding a peptide comprising the isolated peptide of claim 1.

9. An isolated peptide having a length of no more than 22 amino acids and comprising an amino acid sequence comprising at least 90% sequence identity as set forth by SEQ ID NO: 1 with the proviso that the amino acid sequence has a non-phosphorylatable amino acid substitution relative to the serine residue at position 6 of SEQ ID NO: 1.

10. The isolated peptide of claim 9, as set forth by SEQ ID NO:3.

11. The isolated peptide of claim 9, wherein the peptide is BBB-permeant.

12. The isolated peptide of claim 9, wherein the peptide is PEGylated.

13. The isolated peptide of claim 9, further comprising one or more modifications selected from PEGylation, myristoylation, glycosylation, acetylation, phosphorylation, and addition of a linker or spacer.

14. The isolated peptide of claim 9, wherein the peptide is an inverso or retro-inverso peptide.

15. An isolated polynucleotide comprising a nucleic acid sequence encoding a peptide comprising the isolated peptide of claim 9.

16. A method of reducing adverse cardiac effects in a subject, the method comprising administering a therapeutically effective amount of is the isolated peptide of claim 1 to the subject, and wherein administering the isolated peptide reduces occurrence of adverse cardiac effects in the subject.

17. The method of claim 16, wherein the adverse cardiac effects are cardiotoxicity associated with administration of a chemotherapeutic agent to the subject.

18. The method of claim 16, wherein the subject will receive or is receiving a chemotherapeutic agent.

19. The method of claim 16, wherein the peptide has a sequence selected from the group consisting of SEQ ID NO:2, and SEQ ID NO:4.

20. The method of claim 16, wherein the administration is parenteral administration.

21. The method of claim 16, wherein the peptide comprises one or more modifications selected from, PEGylation, myristoylation, glycosylation, acetylation, phosphorylation, and addition of a linker or spacer.

22. The method of claim 16, wherein the peptide is an inverso or retro-inverso peptide.

* * * * *

UNITED STATES PATENT AND TRADEMARK OFFICE
CERTIFICATE OF CORRECTION

PATENT NO.       : 10,858,397 B2
APPLICATION NO.  : 15/756407
DATED            : December 8, 2020
INVENTOR(S)      : Johnathan D. Ebben et al.

Page 1 of 1

It is certified that error appears in the above-identified patent and that said Letters Patent is hereby corrected as shown below:

In the Specification

Column 15, Line 54, "Nw-nitro" should be --Nω-nitro--.

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 7

<210> SEQ ID NO 1
<211> LENGTH: 19
<212> TYPE: PRT
<213> ORGANISM: Homo sapiens

<400> SEQUENCE: 1

Arg Arg Arg Gly Gly Ser Ala Ser Arg Ser Leu Pro Leu Pro Lys Arg
1               5                   10                  15

Pro Arg Arg

<210> SEQ ID NO 2
<211> LENGTH: 19
<212> TYPE: PRT
<213> ORGANISM: Artificial Sequence
<220> FEATURE:
<223> OTHER INFORMATION: phosphomimetic nucXTERT-E

<400> SEQUENCE: 2

Arg Arg Arg Gly Gly Glu Ala Ser Arg Ser Leu Pro Leu Pro Lys Arg
1               5                   10                  15

Pro Arg Arg

<210> SEQ ID NO 3
<211> LENGTH: 19
<212> TYPE: PRT
<213> ORGANISM: Artificial Sequence
<220> FEATURE:
<223> OTHER INFORMATION: phospho-deficient nucXTERT-A

<400> SEQUENCE: 3

Arg Arg Arg Gly Gly Ala Ala Ser Arg Ser Leu Pro Leu Pro Lys Arg
1               5                   10                  15

Pro Arg Arg

<210> SEQ ID NO 4
<211> LENGTH: 22
<212> TYPE: PRT
<213> ORGANISM: Artificial Sequence
<220> FEATURE:
<223> OTHER INFORMATION: PEGylated capped variant nucXTERT

<400> SEQUENCE: 4

Cys Gly Gly Arg Arg Arg Gly Gly Glu Ala Ser Arg Ser Leu Pro Leu
1               5                   10                  15

Pro Lys Arg Pro Arg Arg
            20

<210> SEQ ID NO 5
<211> LENGTH: 20
<212> TYPE: PRT
<213> ORGANISM: Homo sapiens

<400> SEQUENCE: 5

Met Pro Arg Ala Pro Arg Cys Arg Ala Val Arg Ser Leu Leu Arg Ser
1               5                   10                  15

His Tyr Arg Glu
            20

```
<210> SEQ ID NO 6
<211> LENGTH: 19
<212> TYPE: PRT
<213> ORGANISM: Artificial Sequence
<220> FEATURE:
<223> OTHER INFORMATION: variant nucXTERT
<220> FEATURE:
<221> NAME/KEY: VARIANT
<222> LOCATION: (6)..(6)
<223> OTHER INFORMATION: X is Asp or Glu

<400> SEQUENCE: 6

Arg Arg Arg Gly Gly Xaa Ala Ser Arg Ser Leu Pro Leu Pro Lys Arg
1               5                   10                  15

Pro Arg Arg

<210> SEQ ID NO 7
<211> LENGTH: 19
<212> TYPE: PRT
<213> ORGANISM: Artificial Sequence
<220> FEATURE:
<223> OTHER INFORMATION: phosphomimetic aspartic acid peptide

<400> SEQUENCE: 7

Arg Arg Arg Gly Gly Asp Ala Ser Arg Ser Leu Pro Leu Pro Lys Arg
1               5                   10                  15

Pro Arg Arg
```